(12) United States Patent
Jolidon et al.

(10) Patent No.: US 7,442,710 B2
(45) Date of Patent: Oct. 28, 2008

(54) SUBSTITUTED PHENYL METHANONES

(75) Inventors: Synese Jolidon, Blauen (CH); Robert Narquizian, St. Louis (FR); Roger David Norcross, Olsberg (CH); Emmanuel Pinard, Linsdorf (FR)

(73) Assignee: Hoffman-La Roche Inc., Nutley, NJ (US)

( * ) Notice: Subject to any disclaimer, the term of this patent is extended or adjusted under 35 U.S.C. 154(b) by 167 days.

(21) Appl. No.: 11/338,266

(22) Filed: Jan. 24, 2006

(65) Prior Publication Data
US 2006/0167023 A1 Jul. 27, 2006

(30) Foreign Application Priority Data
Jan. 26, 2005 (EP) .................................. 05100473

(51) Int. Cl.
A61K 31/4725 (2006.01)
A61K 31/4741 (2006.01)
A61K 31/4745 (2006.01)
A61K 31/44 (2006.01)
A61K 31/497 (2006.01)
C07D 217/16 (2006.01)
C07D 217/24 (2006.01)
C07D 279/12 (2006.01)
C07D 295/00 (2006.01)
C07D 413/12 (2006.01)
C07D 413/14 (2006.01)
C07D 471/04 (2006.01)
C07D 471/14 (2006.01)
C07D 487/04 (2006.01)
C07D 487/14 (2006.01)
C07D 491/147 (2006.01)
C07D 401/04 (2006.01)
A61P 25/18 (2006.01)
A61K 31/472 (2006.01)
A61K 31/519 (2006.01)
A61K 31/4453 (2006.01)
C07D 215/14 (2006.01)
C07D 471/22 (2006.01)
C07D 487/22 (2006.01)
C07D 491/048 (2006.01)
C07D 491/052 (2006.01)
C07D 491/056 (2006.01)
C07D 491/153 (2006.01)
C07D 491/22 (2006.01)

(52) U.S. Cl. ............... 514/307; 514/264.1; 514/264.11; 514/300; 514/309; 514/310; 514/311; 514/312; 514/313; 514/253.05; 544/58.2; 544/58.6; 544/128; 544/125; 544/126; 544/250; 544/279; 544/363; 546/90; 546/123; 546/141; 546/146; 546/156; 546/165; 546/122; 546/70

(58) Field of Classification Search .................. 514/307, 514/309, 310, 291, 285, 253.05; 546/141, 546/146, 70, 90; 544/58.2, 58.6, 125, 126, 544/128, 363
See application file for complete search history.

(56) References Cited

U.S. PATENT DOCUMENTS
3,933,802 A 1/1976 Ferrini et al.
(Continued)

FOREIGN PATENT DOCUMENTS
EP 0 171 636 2/1985
(Continued)

OTHER PUBLICATIONS
U.S. Appl. No. 10/911,359, filed Aug. 4, 2004, pending.
(Continued)

*Primary Examiner*—Mark L Berch
*Assistant Examiner*—Cecilia M Jaisle
(74) *Attorney, Agent, or Firm*—George W. Johnston; Patricia S. Rocha-Tramaloni; Kimberly J. Prior

(57) ABSTRACT

The present invention relates to compounds of general formula IA or IB

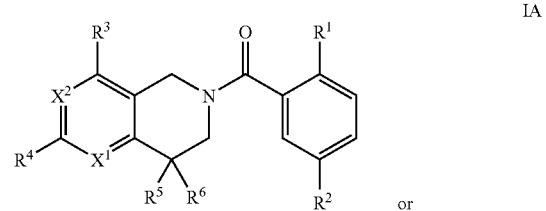

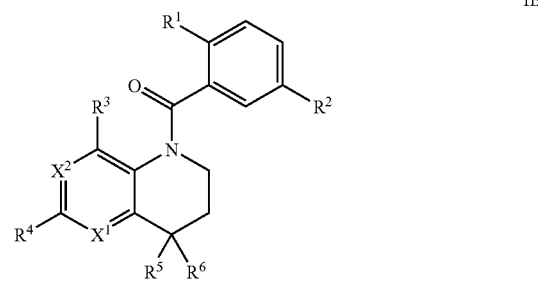

wherein
$X^1$ and $X^2$ are each independently N or C—R" and
$R^1$, $R^2$, $R^3$, $R^4$,
$R^5$, and $R^6$ are as defined in the specification and to pharmaceutically acceptable acid addition salts thereof. The compounds can be used for the treatment of diseases related to the glycine transporter inhibitor, such as schizophrenia and Alzheimer's disease.

19 Claims, No Drawings

U.S. PATENT DOCUMENTS

| | | | |
|---|---|---|---|
| 4,244,871 A | 1/1981 | Kosary et al. | |
| 6,001,854 A | 12/1999 | Ognyanov et al. | |
| 2005/0059668 A1 | 3/2005 | Alberati-Giani et al. | |
| 2005/0070539 A1 | 3/2005 | Alberati-Giani et al. | |
| 2005/0209241 A1 | 9/2005 | Jolidon et al. | |
| 2006/0287308 A1* | 12/2006 | Bird et al. | 514/230.2 |
| 2007/0197565 A1* | 8/2007 | Kelly et al. | 514/264.1 |
| 2007/0197587 A1* | 8/2007 | Ali Awad et al. | 514/312 |
| 2007/0203179 A1* | 8/2007 | Clark et al. | 514/309 |

FOREIGN PATENT DOCUMENTS

| | | |
|---|---|---|
| EP | 0 624 584 | 11/1994 |
| WO | WO 99/44596 | 9/1999 |
| WO | WO 99/45011 | 9/1999 |
| WO | WO 01/81308 | 11/2001 |
| WO | WO 02/22581 A1 | 3/2002 |
| WO | WO 02/22612 | 3/2002 |
| WO | WO 03/004480 | 1/2003 |
| WO | WO 03/035602 | 5/2003 |
| WO | WO 2004/037800 | 5/2004 |
| WO | WO 2004/113301 A1 | 12/2004 |
| WO | WO 2005/058882 | 6/2005 |
| WO | WO 2005/110983 | 11/2005 |

OTHER PUBLICATIONS

U.S. Appl. No. 10/933,103, filed Sep. 2, 2004, pending.
U.S. Appl. No. 10/933,072, filed Sep. 1, 2004, pending.
U.S. Appl. No. 11/291,216, filed Dec. 1, 2005, pending.
U.S. Appl. No. 11/324,990, filed Jan. 3, 2006, pending.
U.S. Appl. No. 11/297,597, filed Dec. 8, 2005, pending.
U.S. Appl. No. 11/302,403, filed Dec. 13, 2005, pending.
U.S. Appl. No. 11/324,991, filed Dec. 3, 2006, pending.
U.S. Appl. No. 11/332,999, filed Jan. 17, 2006, pending.
Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., et al., Cell, vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L., J. Neural Trans. vol. 105, pp. 525-535 (1998).
Kwong et al., Org. Lett. 4, pp. 581-584 (2002).
Kuwano et al., JOC 67, pp. 6479-6486 (2002).
Chem. Abstract XP-002299148.
Caulfield W. L. et al., Journal of Med. Chem. vol. 44(17) pp. 2679-2682 (2001).
Chem. Abstract XP-002299149.
Chemical Abstracts Service, Apr. 23, 2003, XP002308402, Database accession No. 2003: 2142911 Chemcats & Catalog: AsInExExpress Gold.
Chemical Abstracts Service, Jun. 6, 2003, XP002308481 & Database Chemcats.
Chemical Abstracts Service, Jan. 1, 2004, XP002308405, Database accession No. 2003:2872406 Chemcats & Catalog: Ambinter Stock Screening Collection.
Chemical Abstracts Service, Jan. 1, 2004, XP002308403, Database accession No. 2004:591813 & Catalog: Ambinter Stock Screening Collection.
Chemical Abstracts Service, Jan. 1, 2004, XP002308404, Database accession No. 2004:660630 & Catalog: Ambinter Screening Library.
Chemical Abstracts Service, XP002308978.
Chemical Abstracts Service, XP002308979; Chemcats No. 2003:1026314.
Chemical Abstracts Service, XP002308980; Chemcats No. 2001;2814605.
Chemical Abstracts Service, XP002308981; Chemcats No. 2002:2063001.
Chemical Abstracts Service, XP002308983; Chemcats No. 2003:1026533.
Chemical Abstracts Service, XP002308984; Chemcats No. 2002:2288893.
Chemical Abstracts Service, XP002308985; Chemcats No. 2003:709504.
Chemical Abstracts Service, XP002308986; Chemcats No. 2003:709503.
Chemical Abstracts Service, XP002308987; Chemcats No. 2003:709505.
Chemical Abstracts Service, XP002308988; Chemcats No. 2004:1498769.
Chemical Abstracts Service, XP002308989; Chemcats No. 2002:2386068.
Chemical Abstracts Service, XP002308990; Chemcats No. 2002:2894607.
Chemical Abstracts Service, XP002308991; Chemcats No. 2003:3342164.
Chemical Abstracts Service, XP002308992; Chemcats No. 2003:3345505.
Chemical Abstracts Service, XP002308993; Chemcats No. 2003:3346187.
Chemical Abstracts Service, XP002309007; Chemcats No. 2004:660630.
Abstract corresponding to Document B5—WO 03/035602.
Cabiddu et al., Journal of Organometallic Chemistry, 1991, 419(1-2) 1-8.
Collins, et al., J. Med. Chem. 1998, 41, p. 5037-5054.
Yamanaka et al., Tetrahedron Lett., 1996, vol. 37, p. 1829-1832.
Guisado et al., Tetrahedron Lett., 2002, vol. 43, p. 7105-7109.
Souers et al., Bioorganic & Medicinal Chem. Letters, vol. 14(19) pp. 4883-4886 (2004).
Wolin et al., Bioorganic & Medicinal Chem. vol. 12, pp. 4511-4532 (2004).
Lowe, John A., III, Expert Opin. Ther. Patents vol. 15 (11) pp. 1657-1662 (2005).

* cited by examiner

SUBSTITUTED PHENYL METHANONES

PRIORITY TO RELATED APPLICATIONS

This application claims the benefit of European Application No. 05100473.7, filed Jan. 26, 2005, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach poorly address negative and cognitive symptoms which are the predictors of functional outcome (Sharma T., *Br. J. Psychiatry*, 174(suppl. 28): 44-51, 1999).

A complementary model of schizophrenia was proposed in the mid-1960s based upon the psychotomimetic action caused by the blockade of the glutamate system by compounds like phencyclidine (PCP) and related agents (ketamine) which are non-competitive NMDA receptor antagonists. Interestingly, in healthy volunteers, PCP-induced psychotomimetic action incorporates positive and negative symptoms as well as cognitive dysfunction, thus closely resembling schizophrenia in patients (Javitt D C et al., *Biol. Psychiatry*, 45: 668-679, 1999). Furthermore transgenic mice expressing reduced levels of the NMDAR1 subunit display behavioral abnormalities similar to those observed in pharmacologically induced models of schizophrenia, supporting a model in which reduced NMDA receptor activity results in schizophrenia-like behavior (Mohn A R et al., *Cell*, 98: 427-236, 1999).

Glutamate neurotransmission, in particular NMDA receptor activity, plays a critical role in synaptic plasticity, learning and memory, such that NMDA receptors appear to serve as a graded switch for gating the threshold of synaptic plasticity and memory formation (Wiley, N Y; Bliss T V and Collingridge G L, *Nature*, 361: 31-39, 1993). Transgenic mice overexpressing the NMDA NR2B subunit exhibit enhanced synaptic plasticity and superior ability in learning and memory (Tang J P et al., *Natur*, 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters act by removing neurotransmitters from the extracellular space, and can control their extracellular lifetime and thereby modulate the magnitude of the synaptic transmission (Gainetdinov R R et al, *Trends in Pharm. Sci.*, 23(8): 367-373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., *Mol. Mem. Biol.*, 18:13-20, 2001). Thus, one strategy to enhance NMDA receptor activity is to elevate the glycine concentration in the local microenvironment of synaptic NMDA receptors by inhibition of GlyT-1 transporter (Bergereon R. et al., *Proc. Natl. Acad. Sci. USA*, 95:15730-15734, 1998; Chen L. et al., *J. Neurophysiol.*, 89(2): 691-703, 2003).

Glycine transporters inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans,*. 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563-572, 2001).

Thus, increasing activation of NMDA receptors via GlyT-1 inhibition can lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formulae IA and IB

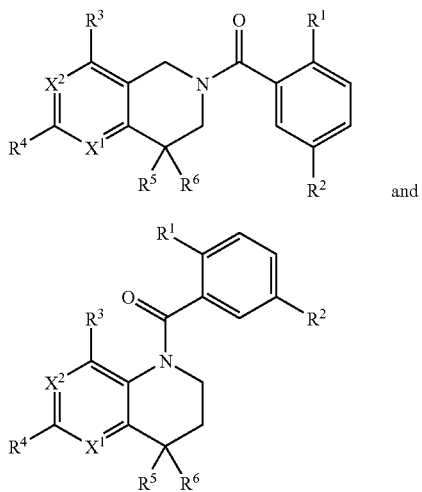

wherein
$R^1$ is aryl, a cyclic amine, $OR^{11}$, $SR^{11}$ or $N(R^{12})_2$;
$R^{11}$ is lower alkyl, lower alkyl substituted by halogen, or $-(CH_2)_n$-cycloalkyl;
each $R^{12}$ is independently hydrogen or lower alkyl;
$R^2$ is $NO_2$, CN or $S(O)_2$-lower alkyl;
$R^3$ is hydrogen, halogen, lower alkyl, lower alkyl substituted by halogen, or lower alkoxy;
$R^4$ is hydrogen, halogen, lower alkyl, lower alkyl substituted by halogen, non cyclic amine, lower alkoxy, or benzyloxy optionally substituted by halogen;
$R^5$ and $R^6$ are each independently hydrogen, halogen, lower alkyl, lower alkoxy, aryl or form together the keto group =O;
$X^1$ is N or C—R';
$X^2$ is N or C—R";
R' is hydrogen, halogen, lower alkyl, lower alkoxy, or benzyloxy optionally substituted by halogen;
R" is hydrogen, alkyl substituted by halogen, halogen, nitro, lower alkoxy, cyano, COO-lower alkyl, benzyloxy optionally substituted by halogen, or $S(O)_2$-cyclic amine; or
$R^3$ and R" or $R^4$ and R' or R" and $R^4$ are together with the carbon atom to which they are attached $-O-(CH_2)_n-O-$ or $-O-(CH_2)_m-$ or $-(CH_2)_m-O-$, or

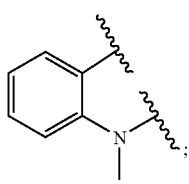

n is 1 or 2; and
m is 2 or 3;
and pharmaceutically acceptable acid addition salts thereof.

The invention also includes all racemic mixtures, all their corresponding enantiomers and/or optical isomers. The present invention also provides pharmaceutical compositions containing one or more compounds of the invention and a pharmaceutically acceptable carrier. The invention further provides methods for the manufacture of compounds and compositions of the invention.

Compounds of formula I are good inhibitors of the glycine transporter 1 (GlyT-1), and have a good selectivity to glycine transporter 2 (GlyT-2) inhibitors. The present invention further provides methods for the treatment of diseases related to activation of NMDA receptors via Glyt-1 inhibition, such as psychoses, dysfunction in memory and learning, schizophrenia, dementia and other diseases in which cognitive processes are impaired, such as attention deficit disorders or Alzheimer's disease. The preferred indications using the compounds of the present invention are schizophrenia, cognitive impairment and Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-carbon chain containing from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "cycloalkyl" denotes a saturated carbon ring, containing from 3 to 6 carbon atoms.

The term "halogen" denotes chlorine, fluorine, bromine, and iodine.

The term "alkyl substituted by halogen" denotes a saturated straight- or branched-carbon chain containing from 1 to 6 carbon atoms as defined above for "alkyl" wherein at least one hydrogen atom is replaced by a halogen atom, for example $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$. Preferred are $CH_2CF_3$ or $CF_3$.

The term "lower alkoxy" denotes a saturated straight- or branched-carbon chain containing from 1 to 6 carbon atoms as described above which is connected via an oxygen atom.

The term "cyclic amine" denotes a 5-7 membered non aromatic cyclic group, containing at least one N-atom which can contain in addition to the N atom a further heteroatom, selected from N, O or S, for example pyrrol-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl.

The term "aryl" denotes a monovalent cyclic aromatic hydrocarbon group consisting of one or more rings in which at least one ring is aromatic in nature, for example phenyl or naphthyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides compounds of formulae IA and IB

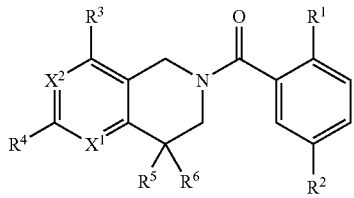

and

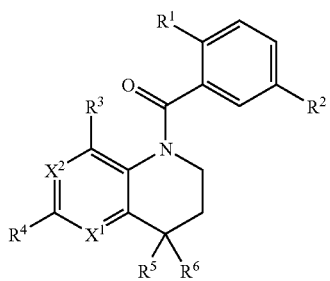

wherein
$R^1$ is aryl, a cyclic amine, $OR^{11}$, $SR^{11}$ or $N(R^{12})_2$;
$R^{11}$ is lower alkyl, lower alkyl substituted by halogen or —$(CH_2)_n$-cycloalkyl;
each $R^{12}$ is independently hydrogen or lower alkyl;
$R^2$ is $NO_2$, CN or $S(O)_2$-lower alkyl;
$R^3$ is hydrogen, halogen, lower alkyl, lower alkyl substituted by halogen, or lower alkoxy-,
$R^4$ is hydrogen, halogen, lower alkyl, lower alkyl substituted by halogen, non cyclic amine, lower alkoxy, or benzyloxy optionally substituted by halogen;
$R^5$ and $R^6$ are each independently hydrogen, halogen, lower alkyl, lower alkoxy, aryl or form together the keto group =O;
$X^1$ is N or C—R';
$X^2$ is N or C—R";
R' is hydrogen, halogen, lower alkyl, lower alkoxy, or benzyloxy optionally substituted by halogen;
R" is hydrogen, alkyl substituted by halogen, halogen, nitro, lower alkoxy, cyano, COO-lower alkyl, benzyloxy optionally substituted by halogen, or $S(O)_2$-cyclic amine; or
$R^3$ and R" or $R^4$ and R' or R" and $R^4$ are together with the carbon atom to which they are attached —O—$(CH_2)_n$—O— or —O—$(CH_2)_m$— or —$(CH_2)_m$—O—, or

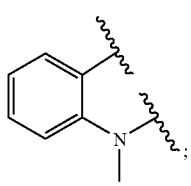

n is 1 or 2; and
m is 2 or 3;
and pharmaceutically acceptable acid addition salts thereof.

In particular, the invention provides the following compounds of formula I:

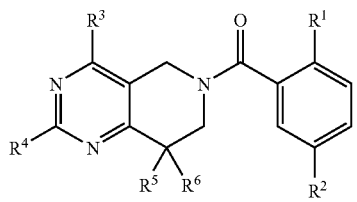

or

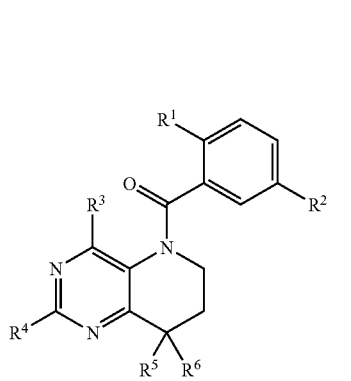

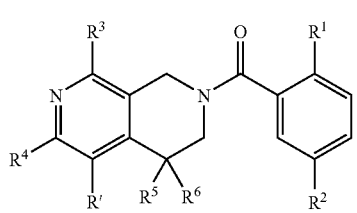

or

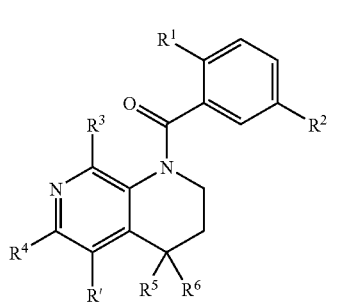

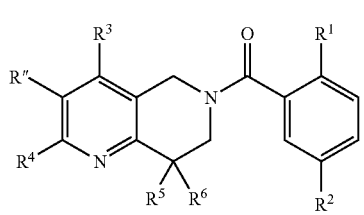

or

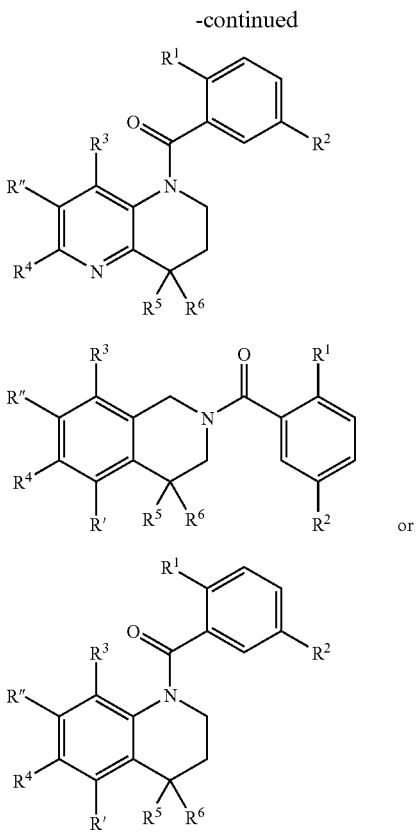

wherein

R¹ is aryl, a cyclic amine, OR¹¹, SR¹¹ or N(R¹²)₂;
R¹¹ is lower alkyl, lower alkyl substituted by halogen, or —(CH₂)ₙ-cycloalkyl;
each R¹² is independently hydrogen or lower alkyl;
R² is NO₂, CN or S(O)₂-lower alkyl;
R³ is hydrogen, halogen, lower alkyl, lower alkyl substituted by halogen, or lower alkoxy;
R⁴ is hydrogen, halogen, lower alkyl, lower alkyl substituted by halogen, non cyclic amine, lower alkoxy, or benzyloxy optionally substituted by halogen;
R⁵ and R⁶ are each independently hydrogen, halogen, lower alkyl, lower alkoxy, aryl, or form together the keto group =O;
R' is hydrogen, halogen, lower alkyl, lower alkoxy, or benzyloxy optionally substituted by halogen;
R" is hydrogen, alkyl substituted by halogen, halogen, nitro, lower alkoxy, cyano, COO-lower alkyl, benzyloxy optionally substituted by halogen, or S(O)₂-cyclic amine; or
R³ and R" or R⁴ and R' or R" and R⁴ are together with the carbon atom to which they are attached —O—(CH₂)ₙ—O— or —O—(CH₂)ₘ— or —(CH₂)ₘ—O—, or

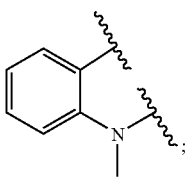

n is 1 or 2; and
m is 2 or 3;
and pharmaceutically acceptable acid addition salts thereof.

For example, the invention provides compounds of formula IA-1 or IB-1. Alternatively, the invention provides compounds of formula IA-2 or IB-2. The invention also provides compounds of formula IA-3 or IB-3. The invention further provides compounds of formula IA-4 or IB-4.

Preferred compounds of formula I are those in which R² is SO₂CH₃. In particular, such compounds in which R¹ is OR¹¹ are preferred. Also preferred within this group are compounds in which R¹ is aryl, for example, phenyl. Further preferred within this group are compounds in which R¹ is a cyclic amine.

Most preferred compounds of formula I are those of formula IA-4.

Especially preferred are compounds of this group, wherein at least one of R³, R", R⁴ or R' is halogen, for example
(6-chloro-3,4-dihydro-1H-isoquinolin-2-yl)-[5-methane-sulfonyl-2-((S)-2,2,2-trifluoro-1-methyl-ethoxy)-phenyl]-methanone,
(6-chloro-3,4-dihydro-1H-isoquinolin-2-yl)-(2-isopropoxy-5-methanesulfonyl-phenyl)-methanone,
(7-chloro-3,4-dihydro-1H-isoquinolin-2-yl)-(2-isopropoxy-5-methanesulfonyl-phenyl)-methanone,
(7,8-dichloro-3,4-dihydro-1H-isoquinolin-2-yl)-(2-isopropoxy-5-methanesulfonyl-phenyl)-methanone and
(8-chloro-3,4-dihydro-1H-isoquinolin-2-yl)-(2-isopropoxy-5-methanesulfonyl-phenyl)-methanone.

Further preferred are compounds of this group, wherein at least one of R³, R", R⁴ or R' is alkyl substituted by halogen, for example
(2-isopropoxy-5-methanesulfonyl-phenyl)-(6-trifluoromethyl-3,4-dihydro-1H-isoquinolin-2-yl)-methanone,
(5-methanesulfonyl-2-morpholin-4-yl-phenyl)-(6-trifluoromethyl-3,4-dihydro-1H-isoquinolin-2-yl)-methanone,
[5-methanesulfonyl-2-((S)-2,2,2-trifluoro-1-methyl-ethoxy)-phenyl]-(6-trifluoromethyl-3,4-dihydro-1H-isoquinolin-2-yl)-methanone and
(4-methanesulfonyl-biphenyl-2-yl)-(6-trifluoromethyl-3,4-dihydro-1H-isoquinolin-2-yl)-methanone.

Further preferred are compounds of this group, wherein at least one of R³, R", R⁴ or R' is CN, for example
2-(2-isopropoxy-5-methanesulfonyl-benzoyl)-1,2,3,4-tetrahydro-isoquinoline-6-carbonitrile.

Further preferred are compounds of this group, wherein at least one of R³, R", R⁴ or R' is lower alkoxy, for example
(2-isopropoxy-5-methanesulfonyl-phenyl)-(6-methoxy-3,4-dihydro-1H-isoquinolin-2-yl)-methanone.

A further preferred group of compounds of formula IA-4 are those, wherein R' is S-lower alkyl, for example
(6-chloro-3,4-dihydro-1H-isoquinolin-2-yl)-(2-isopropylsulfanyl-5-methanesulfonyl-phenyl)-methanone.

Preferred are further compounds, wherein one of R³ and R" or R⁴ and R' or R" and R⁴ are together with the carbon atom to which they are attached —O—CH₂—O— or

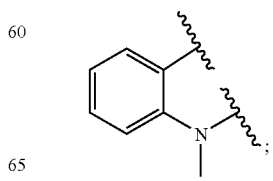

for example the following compounds:
(2-isopropoxy-5-methanesulfonyl-phenyl)-(11-methyl-1,2, 4,11-tetrahydro-pyrido[4,3-a]carbazol-3-yl)-methanone and
((4,9-dimethyl-7,8-dihydro-5H-[1,3]dioxolo[4,5-g]isoquinolin-6-yl)-(2-isopropoxy-5-methanesulfonyl-phenyl)-methanone.

A preferred group of compounds are those from formula IA-3, for example
(4-methanesulfonyl-biphenyl-2-yl)-(2-trifluoromethyl-7,8-dihydro-5H-[1,6]naphthyridin-6-yl)-methanone.

The present compounds of formula I and their pharmaceutically acceptable salts can be prepared by methods known in the art, for example, by processes described below, which process comprises a) reacting a compound of formula IIA or IIB

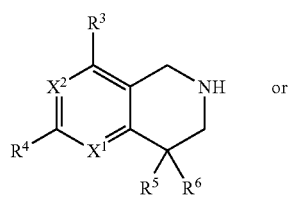  IIA

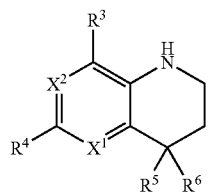  IIB with a compound of formula III

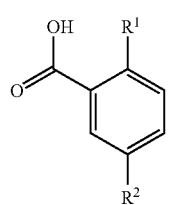  III in the presence of an activating agent, such as TBTU (2-(1H-benzotriazole-1-yl)-1,1,3,3-tetramethyluroniumtetrafluoroborate), to produce a compound of formula IA or IB

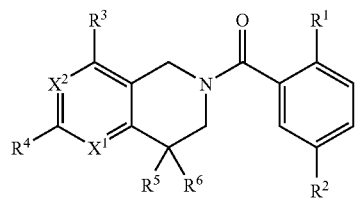  IA

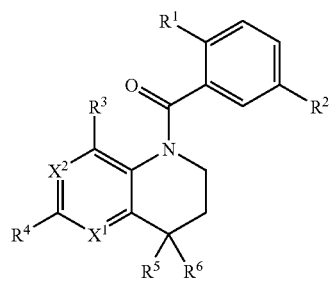  IB wherein the substituents are as defined above, or b) reacting a compound of formula

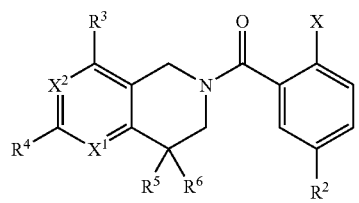  IV A

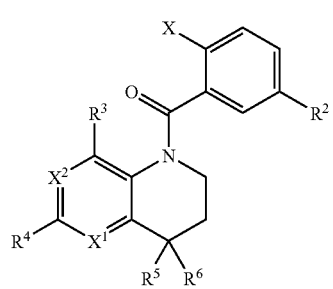  IV B with a compound of formula $R^{11}OH$, optionally in the presence of a catalyst, such as Cu(I)I, and a base, like potassium carbonate, cesium carbonate or sodium, to produce a compound of formula IA1 or IB1

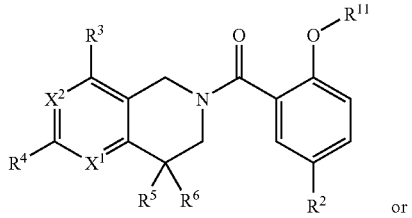

IA1

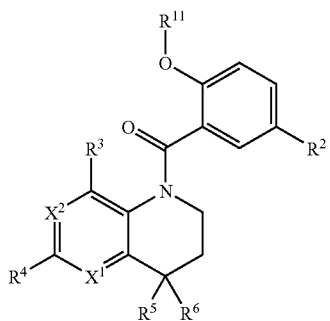

IB1 wherein X is halogen, the other substituents are as defined above, or c) reacting a compound of formula

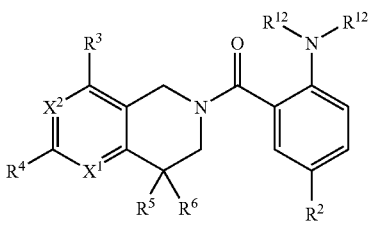

IV A

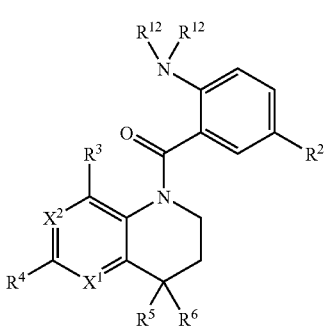

IV B with a compound of formula

NH(R$^{12}$)$_2$ or with a cyclic amine, optionally in the presence of a catalyst, such as Cu(I)I, and a base, like potassium carbonate, cesium carbonate or sodium, to produce a compound of formula IA10 or IB10

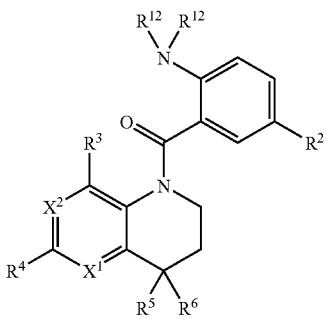

IA10

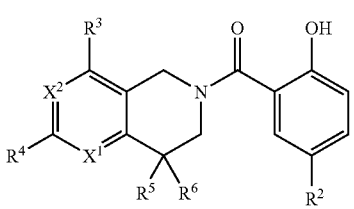

IB10 wherein X is halogen, R$^{12}$ is as defined above or the two R$^{12}$ together with the N-atom can form a cyclic amine and the other substituents are as defined above, or d) reacting a compound of formula

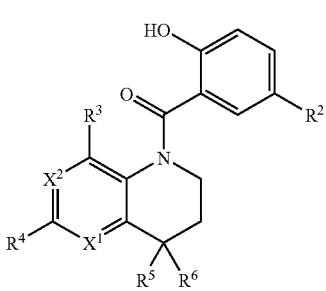

VA

VB with a compound of formula

R$^{11}$X in the presence of a base and optionally in the presence of microwaves to produce a compound of formula IA1 or IB1

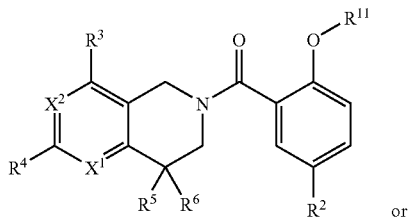

IA1

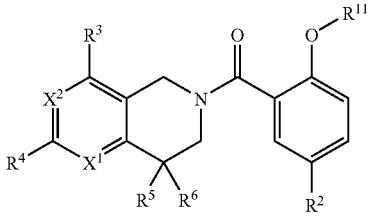

IA1

IB1

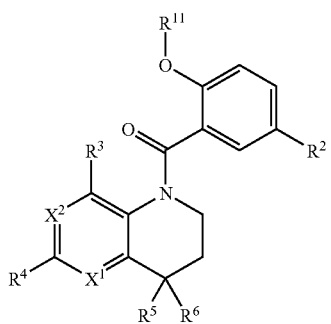

IB1

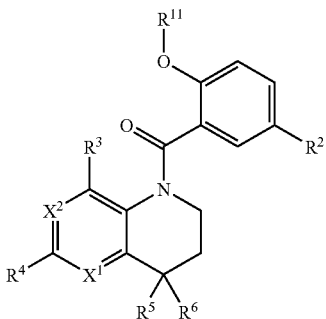

wherein X is halogen, mesylate or triflate and $R^{11}$ is lower alkyl, lower alkyl substituted by halogen, or $(CH_2)_n$-cycloalkyl: or e) reacting a compound of formula

VA

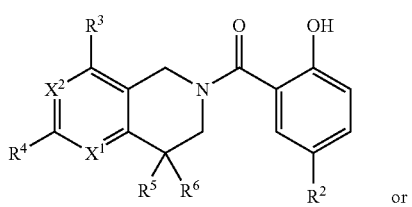

or

VB

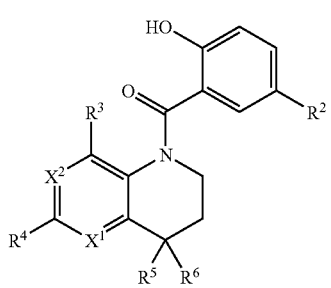

with a compound of formula $R^{11}OH$ under Mitsunobu conditions in the presence of a phosphine to produce a compound of formula wherein the substituents are as defined above.

Compounds of the formula IIA or IIB, IVA or IVB, VA or VB or VII are either commercially available, their preparation is described in the chemical literature or they can be prepared by methods known in the art.

Compounds of formula III can be prepared as follow:

Scheme 1

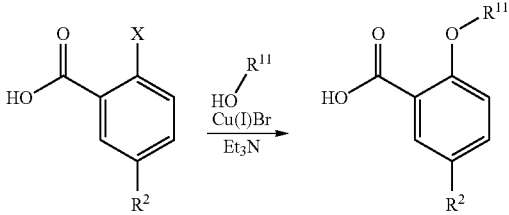

where X = halogen

For example, compounds of formula IIIa where $R^{11}$ is lower alkyl, lower alkyl, substituted by halogen or —$(CH_2)_n$-cycloalkyl, can be prepared by reaction of a halogen compound of formula VI with an alcohol of formula $R^{11}OH$, optionally in the presence of a copper salt, like Cu(I)Br, and a base, such as triethylamine (Scheme 1), at elevated temperature.

Scheme 2

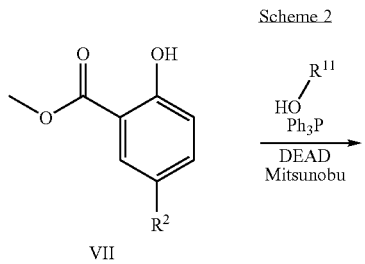

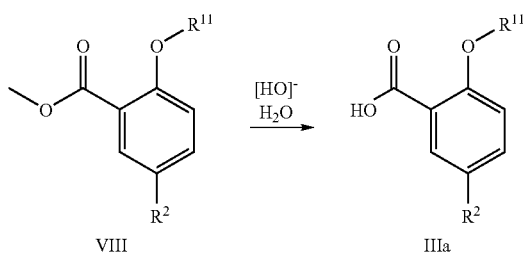

Alternatively, compounds of formula IIIa, where $R^{11}$ is lower alkyl, lower alkyl, substituted by halogen or —$(CH_2)_n$-cycloalkyl can be prepared by reacting a hydroxy compound of formula VII with an alcohol of formula $R^{11}OH$, under Mitsunobu reaction conditions in the presence of a phosphine, like triphenylphosphine or diphenyl-2-pyridylphosphine, and a dialkylazadicarboxylate, like diethylazadicarboxylate or di-tert-butyl azodicarboxylate, to afford intermediate compounds of formula VIII, followed by hydrolysis in the presence of an aqueous base, such as potassium hydroxide, sodium hydroxide or lithium hydroxide (Scheme 2).

Scheme 3

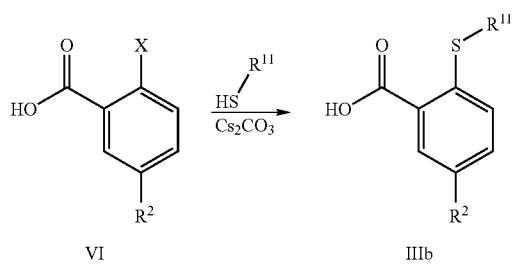

Compounds of formula IIIb where $R^{11}$ is lower alkyl, lower alkyl, substituted by halogen or —$(CH_2)_n$-cycloalkyl, can be prepared by reaction of a halogen compound of formula VI with a thiol of formula $R^{11}SH$, optionally in the presence of a base, such as cesium carbonate, potassium carbonate or sodium carbonate (Scheme 3), at elevated temperature.

Scheme 4

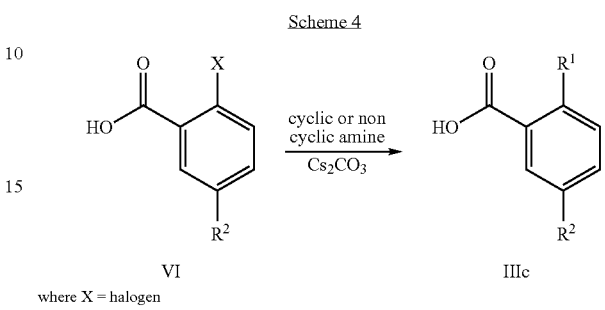

Compounds of formula IIIc where $R^1$ is a cyclic amine or $NH(R^{12})_2$, can be prepared by reaction of a halogen compound of formula VI with an amine, optionally in the presence of a base, such as cesium carbonate, potassium carbonate or sodium carbonate (Scheme 4), at elevated temperature.

The halogen-substituted and hydroxy-substituted starting materials of formula VI are either commercially available, are otherwise known in the chemical literature, or can be prepared using a variety of methods well known in the art.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I can be basic, for example in cases where the residue $R^1$ contains a basic group such as an aliphatic or aromatic amine moiety. In such cases the compounds of formula I can be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention are good inhibitors of the glycine transporter 1 (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies).

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose. Flp-in™-CHO (Invitrogen Cat n° R758-07) cells stably transfected with mGlyT1b cDNA.

Glycine uptake inhibition assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The preferred compounds show an $IC_{50}$ (µM) at GlyT-1 in the range of 0.040-0.500.

Representative compounds are shown in the table below.

| Example No. | $IC_{50}$ (µM) |
| --- | --- |
| 1.8 | 0.082 |
| 1.12 | 0.046 |
| 1.13 | 0.321 |
| 1.14 | 0.175 |
| 1.15 | 0.168 |
| 1.18 | 0.157 |
| 1.19 | 0.359 |
| 1.20 | 0.454 |
| 1.25 | 0.215 |
| 1.26 | 0.163 |
| 1.30 | 0.344 |
| 1.40 | 0.481 |
| 1.47 | 0.159 |
| 1.53 | 0.483 |
| 1.57 | 0.160 |

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

Compounds of formula I are good inhibitors of the glycine transporter 1 (GlyT-1), and have good selectivity to glycine transporter 2 (GlyT-2) inhibitors. The invention further provides methods for the treatment of diseases related to activation of NMDA receptors via Glyt-1 inhibition, such as psychoses, dysfunction in memory and learning, schizophrenia, dementia and other diseases in which cognitive processes are impaired, such as attention deficit disorders or Alzheimer's disease. In particular, the present invention provides a method for treating schizophrenia, which comprises administering a therapeutically effective amount of a compound of formula I or a pharmaceutically acceptable salt thereof. The invention also provides a method of treating cognitive impairment, which comprises administering a therapeutically effective amount of a compound of formula I or a pharmaceutically acceptable salt thereof. The invention further provides a method for the treatment of Alzheimer's disease, which comprises administering a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Experimental Part

All starting materials are either commercially available, described in the literature (CA-abstract-numbers are given) or can be prepared by methods well known in the art.

The following abbreviations have been used:
TBTU=2-(1H-Benzotriazole-1-yl)-1,1,3,3-tetramethyluroniumtetrafluoroborate
DIPEA=Ethyl-diisopropyl-amine
Oxone®=potassium peroxymonosulfate $2KHSO_5 \cdot KHSO_4 \cdot K_2SO_4$

EXAMPLE 1.1

Preparation of (2-Isopropoxy-5-methanesulfonyl-phenyl)-(2-trifluoromethyl-7,8-dihydro-5H-pyrido[4,3-d]pyrimidin-6-yl)-methanone

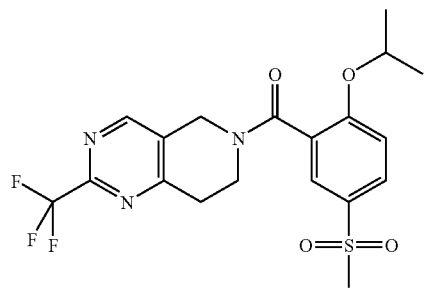

A solution of 0.23 mmol 2-trifluoromethyl-5,6,7,8-tetrahydro-pyrido[4,3-d]pyrimidine (CA [74737-17-7]; WO2004069162), 0.23 mmol 2-isopropoxy-5-methanesulfonyl-benzoic acid (Example 2.1) and 1.1 mmol of DIPEA in 5 ml of acetonitrile was treated with 0.25 mmol TBTU. The reaction mixture was stirred at room temperature for one hour, concentrated and hydrolyzed with 5 ml of water. Extraction with ethyl acetate yields a crude product which is purified by chromatography (SiO$_2$; ethyl acetate) to give, after trituration in diethyl ether, the title compound as a colorless solid. Yield=83%.
MS (m/e): 444.4 (M+H$^+$).

EXAMPLE 1.2

Preparation of [5-Methanesulfonyl-2-((R)-2,2,2-trifluoro-1-methyl-ethoxy)-phenyl]-(2-trifluoromethyl-7,8-dihydro-5H-pyrido[4,3-d]pyrimidin-6-yl)-methanone

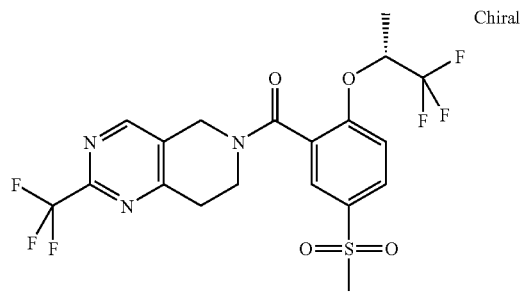

Prepared in analogy to example 1.1 from 2-trifluoromethyl-5,6,7,8-tetrahydro-pyrido[4,3-d]pyrimidine (CA [74737-17-7]; WO2004069162) and 5-methanesulfonyl-2-((R)-2,2,2-trifluoro-1-methyl-ethoxy)-benzoic acid (example 2.3). MS (m/e): 498.4 (M+H$^+$).

EXAMPLE 1.3

Preparation of [5-Methanesulfonyl-2-((S)-2,2,2-trifluoro-1-methyl-ethoxy)-phenyl]-(2-trifluoromethyl-7,8-dihydro-5H-pyrido[4,3-d]pyrimidin-6-yl)-methanone

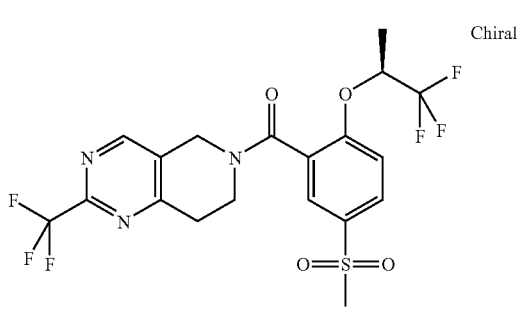

Prepared in analogy to example 1.1 from 2-trifluoromethyl-5,6,7,8-tetrahydro-pyrido[4,3-d]pyrimidine (CA [74737-17-7]; WO2004069162) and 5-methanesulfonyl-2-((S)-2,2,2-trifluoro-1-methyl-ethoxy)-benzoic acid (example 2.2). MS (m/e): 498.4 (M+H$^+$).

EXAMPLE 1.4

Preparation of (4-Methanesulfonyl-biphenyl-2-yl)-(2-trifluoromethyl-7,8-dihydro-5H-pyrido[4,3-d]pyrimidin-6-yl)-methanone

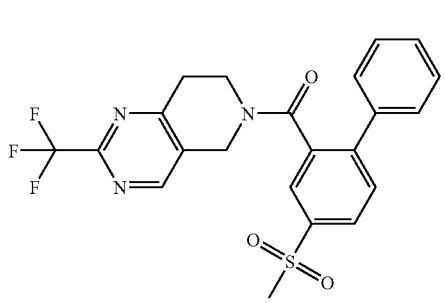

Prepared in analogy to example 1.1 from 2-trifluoromethyl-5,6,7,8-tetrahydro-pyrido[4,3-d]pyrimidine (CA [74737-17-7]; WO2004069162) and 4-methanesulfonyl-biphenyl-2-carboxylic acid (example 2.5). MS (m/e): 462.0 (M+H$^+$).

EXAMPLE 1.5

Preparation of (2-Isopropoxy-5-methanesulfonyl-phenyl)-(2-trifluoromethyl-7,8-dihydro-5H-[1,6]naphthyridin-6-yl)-methanone

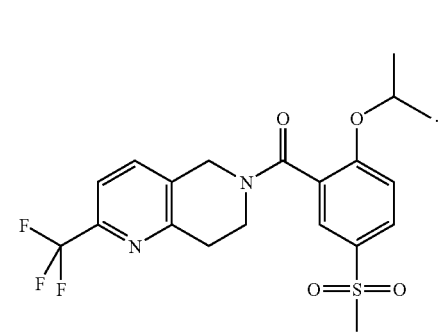

Prepared in analogy to example 1.1 from 2-trifluoromethyl-5,6,7,8-tetrahydro-[1,6]naphthyridine hydrochloride (CA [741736-98-1]; WO2004069162) and 2-isopropoxy-5-methanesulfonyl-benzoic acid (Example 2.1). MS (m/e): 443.5 (M+H$^+$).

EXAMPLE 1.6

Preparation of [5-Methanesulfonyl-2-((S)-2,2,2-trifluoro-1-methyl-ethoxy)-phenyl]-(2-trifluoromethyl-7,8-dihydro-5H-[1,6]naphthyridin-6-yl)-methanone

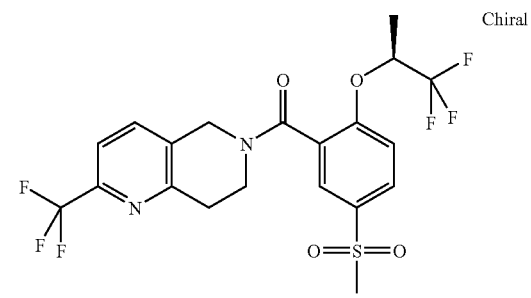

Prepared in analogy to example 1.1 from 2-trifluoromethyl-5,6,7,8-tetrahydro-[1,6]naphthyridine hydrochloride (CA [741736-98-1]; WO2004069162) and 5-methanesulfonyl-2-((S)-2,2,2-trifluoro-1-methyl-ethoxy)-benzoic acid (example 2.2).

MS (m/e): 497.5 (M+H$^+$).

EXAMPLE 1.7

Preparation of [5-Methanesulfonyl-2-((R)-2,2,2-trifluoro-1-methyl-ethoxy)-phenyl]-(2-trifluoromethyl-7,8-dihydro-5H-[1,6]naphthyridin-6-yl)-methanone

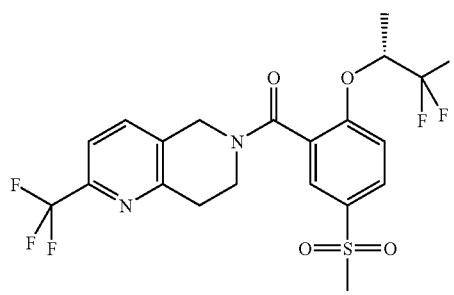

Prepared in analogy to example 1.1 from 2-trifluoromethyl-5,6,7,8-tetrahydro-[1,6]naphthyridine hydrochloride (CA [741736-98-1]; WO2004069162) and 5-methanesulfonyl-2-((R)-2,2,2-trifluoro-1-methyl-ethoxy)-benzoic acid (example 2.3).

MS (m/e): 497.5 (M+H$^+$).

EXAMPLE 1.8

Preparation of (4-Methanesulfonyl-biphenyl-2-yl)-(2-trifluoromethyl-7,8-dihydro-5H-[1,6]naphthyridin-6-yl)-methanone

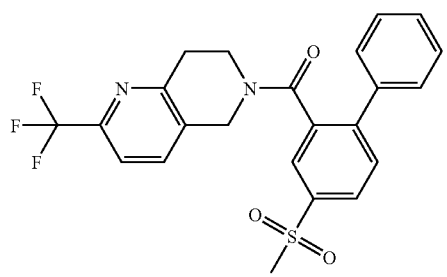

Prepared in analogy to example 1.1 from 2-trifluoromethyl-5,6,7,8-tetrahydro-[1,6]naphthyridine hydrochloride (CA [741736-98-1]; WO2004069162) and 4-methanesulfonyl-biphenyl-2-carboxylic acid (example 2.5). MS (m/e): 461.3 (M+H$^+$).

EXAMPLE 1.9

Preparation of 6-[5-Methanesulfonyl-2-((S)-2,2,2-trifluoro-1-methyl-ethoxy)-benzoyl]-2-trifluoromethyl-5,6,7,8-tetrahydro-[1,6]naphthyridine-3-carboxylic acid ethyl ester

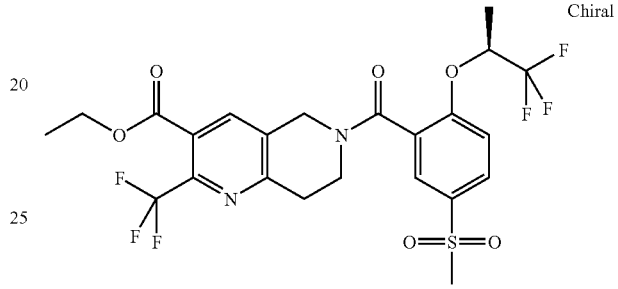

Prepared in analogy to example 1.1 from 2-trifluoromethyl-5,6,7,8-tetrahydro-[1,6]naphthyridine-3-carboxylic acid ethyl ester hydrochloride (CA [741736-90-3]; WO2004069162) and 5-methanesulfonyl-2-((S)-2,2,2-trifluoro-1-methyl-ethoxy)-benzoic acid (example 2.2). MS (m/e): 569.0 (M+H$^+$).

EXAMPLE 1.10

Preparation of 6-[5-Methanesulfonyl-2-((R)-2,2,2-trifluoro-1-methyl-ethoxy)-benzoyl]-2-trifluoromethyl-5,6,7,8-tetrahydro-[1,6]naphthyridine-3-carboxylic acid ethyl ester

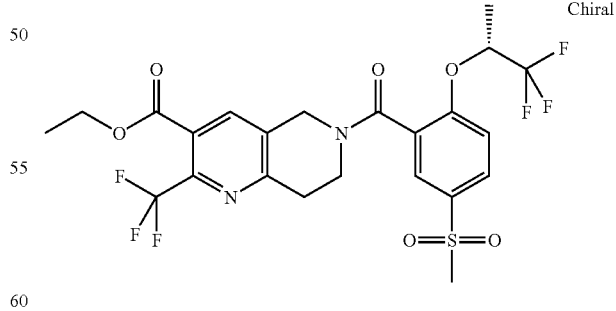

Prepared in analogy to example 1.1 from 2-trifluoromethyl-5,6,7,8-tetrahydro-[1,6]naphthyridine-3-carboxylic acid ethyl ester hydrochloride (CA [741736-90-3]; WO2004069162) and 5-methanesulfonyl-2-((R)-2,2,2-trifluoro-1-methyl-ethoxy)-benzoic acid (example 2.3). MS (m/e): 569.0 (M+H$^+$).

EXAMPLE 1.11

Preparation of [5-Methanesulfonyl-2-((S)-2,2,2-trifluoro-1-methyl-ethoxy)-phenyl]-(2-methoxy-7,8-dihydro-5H-pyrido[4,3-d]pyrimidin-6-yl)-methanone (a) 2-Methoxy-7,8-dihydro-5H-pyrido[4,3-d]pyrimidine-6-carboxylic acid tert-butyl ester

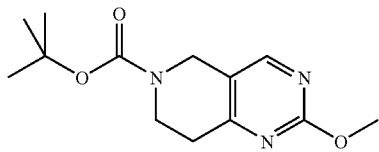

A mixture of 8.0 mmol 3-dimethylaminomethylene-4-oxo-piperidine-1-carboxylic acid tert-butyl ester (CA [157327-41-8]) and 10 mmol O-methylisourea hydrochloride in 25 ml ethanol is treated with 11 mmol triethylamine and 5 drops of water. The suspension is refluxed overnight, concentrated and diluted with 100 ml water. Extraction with ethyl acetate and chromatography (SiO$_2$; ethyl acetate/n-heptane 1:1) gives the title compound as a yellowish oil.

Yield=28%. MS (m/e): 266.3 (M+H$^+$).

(b) 2-Methoxy-5,6,7,8-tetrahydro-pyrido[4,3-d]pyrimidine

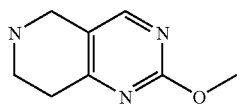

2 mmol 2-Methoxy-7,8-dihydro-5H-pyrido[4,3-d]pyrimidine-6-carboxylic acid tert-butyl ester is dissolved in 15 ml dichloromethane and 10 mmol trifluoroacetic acid is added. The reaction mixture is stirred for 30 minutes at 40° C., concentrated and neutralized by addition of aqueous sodium carbonate. Extraction with ethyl acetate yields the crude title compound as a brownish oil. MS (m/e): 166.4 (M+H$^+$).

(c) [5-Methanesulfonyl-2-((S)-2,2,2-trifluoro-1-methyl-ethoxy)-phenyl]-(2-methoxy-7,8-dihydro-5H-pyrido[4,3-d]pyrimidin-6-yl)-methanone

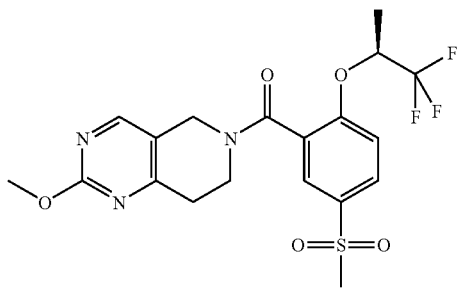

Prepared in analogy to example 1.1 from 2-methoxy-5,6,7,8-tetrahydro-pyrido[4,3-d]pyrimidine and 5-methanesulfonyl-2-((S)-2,2,2-trifluoro-1-methyl-ethoxy)-benzoic acid (example 2.2). MS (m/e): 460.4 (M+H$^+$).

EXAMPLE 1.12

Preparation of (2-Isopropoxy-5-methanesulfonylphenyl)-(6-trifluoromethyl-3,4-dihydro-1H-isoquinolin-2-yl)-methanone (a) 2,2,2-Trifluoro-N-[2-(3-trifluoromethyl-phenyl)-ethyl]-acetamide

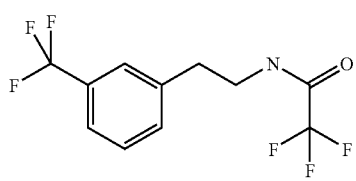

A solution of 14 mmol 2-(3-trifluoromethylphenyl)-ethylamine in 10 ml dichloromethane is slowly added with stirring over 15 minutes to an ice-cooled solution of 42 mmol trifluoroacetic anhydride in 10 ml dichloromethane. After completion of the addition, the reaction mixture is stirred for additional 2 hours at room temperature, then poured into 100 ml of water. The pH is carefully adjusted to 7 by addition of solid sodium hydrogencarbonate. The organic layer is dried and concentrated to give the title compound as a colorless oil which solidifies upon standing. Yield=94%. MS (m/e): 284.1 (M–H$^+$).

(b) 2,2,2-Trifluoro-1-(6-trifluoromethyl-3,4-dihydro-1H-isoquinolin-2-yl)-ethanone and 2,2,2-Trifluoro-1-(8-trifluoromethyl-3,4-dihydro-1H-isoquinolin-2-yl)-ethanone

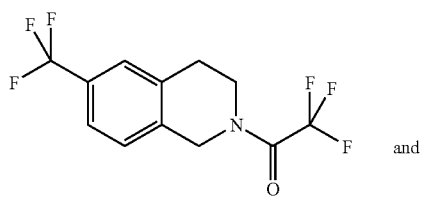

and

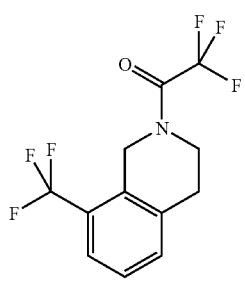

15 ml of acetic acid are slowly added to 20 ml of concentrated (97%) sulfuric acid; the reaction is strongly exothermic. After cooling to room temperature, 11 mmol of ,2,2-trifluoro-N—

[2-(3-trifluoromethyl-phenyl)-ethyl]-acetamide and 16 mmol of paraformaldehyde is added. The solution is stirred overnight at room temperature, then poured into 100 ml of an ice water mixture. Extraction with ethyl acetate yields the crude product, consisting of a mixture of the two title regioisomers. Chromatography (SiO$_2$; ethyl acetate/cyclohexane 1:9) yields 2,2,2-trifluoro-1-(6-trifluoromethyl-3,4-dihydro- 1H-isoquinolin-2-yl)-ethanone as the most rapidly eluting fraction. Yield of the colorless solid=43%. MS (m/e): 297.1 (M−H⁺).

The compound with longer elution times is the 2,2,2-trifluoro-1-(8-trifluoromethyl-3,4-dihydro-1H-isoquinolin-2-yl)-ethanone. Colorless solid. Yield=30%.

MS (m/e): 297.1 (M+H⁺).

(c) 6-Trifluoromethyl-1,2,3,4-tetrahydro-isoquinoline

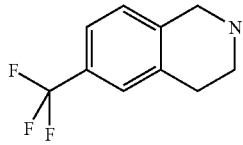

A solution of 4 mmol 2,2,2-trifluoro-1-(6-trifluoromethyl-3,4-dihydro-1H-isoquinolin-2-yl)-ethanone in 12 ml ethanol is treated with 11 ml of 2M aqous sodium hydroxide. The reaction mixture is stirred for 1 hour at room temperature, concentrated, diluted with water and extracted 3 times with ethyl acetate to give the title compound as a yellowish oil. Yield=83%. MS (m/e): 202.2 (M+H⁺).

(d) (2-Isopropoxy-5-methanesulfonyl-phenyl)-(6-trifluoromethyl-3,4-dihydro-1H-isoquinolin-2-yl)-methanone

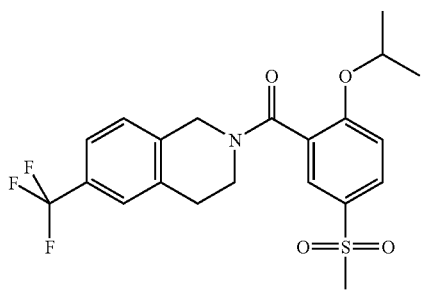

Prepared in analogy to example 1.1 from 6-trifluoromethyl-1,2,3,4-tetrahydro-isoquinoline and 2-isopropoxy-5-methanesulfonyl-benzoic acid (Example 2.1).

MS (m/e): 442.1 (M+H⁺).

EXAMPLE 1.13

Preparation of (5-Methanesulfonyl-2-morpholin-4-yl-phenyl)-(6-trifluoromethyl-3,4-dihydro-1H-isoquinolin-2-yl)-methanone

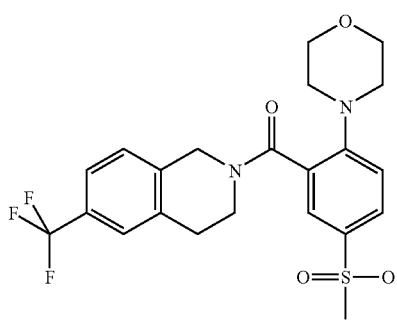

Prepared in analogy to example 1.1 from 6-trifluoromethyl-1,2,3,4-tetrahydro-isoquinoline and 5-methanesulfonyl-2-morpholin-4-yl-benzoic acid (Example 2.4).

MS (m/e): 469.5 (M+H⁺).

EXAMPLE 1.14

Preparation of [5-Methanesulfonyl-2-((S)-2,2,2-trifluoro-1-methyl-ethoxy)-phenyl]-(6-trifluoromethyl-3,4-dihydro-1H-isoquinolin-2-yl)-methanone

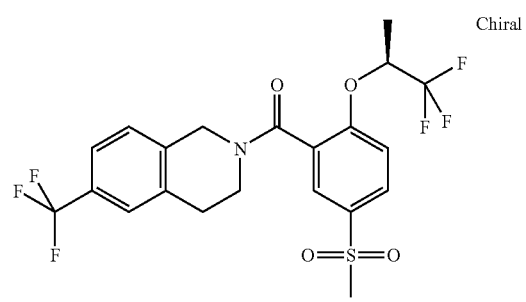

Prepared in analogy to example 1.1 from 6-trifluoromethyl-1,2,3,4-tetrahydro-isoquinoline and 5-methanesulfonyl-2-((S)-2,2,2-trifluoro-1-methyl-ethoxy)-benzoic acid (example 2.2). MS (m/e): 496.0 (M+H⁺).

EXAMPLE 1.15

Preparation of (4-Methanesulfonyl-biphenyl-2-yl)-(6-trifluoromethyl-3,4-dihydro-1H-isoquinolin-2-yl)-methanone

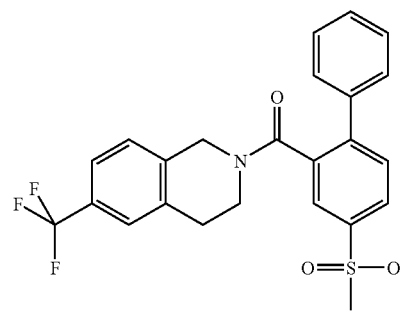

Prepared in analogy to example 1.1 from 6-trifluoromethyl-1,2,3,4-tetrahydro-isoquinoline and 4-methanesulfonyl-biphenyl-2-carboxylic acid (example 2.5).

MS (m/e): 460.1 (M+H⁺).

EXAMPLE 1.16

Preparation of (2-Isopropoxy-5-methanesulfonyl-phenyl)-(8-trifluoromethyl-3,4-dihydro-1H-isoquinolin-2-yl)-methanone (a) 8-Trifluoromethyl-1,2,3,4-tetrahydro-isoquinoline

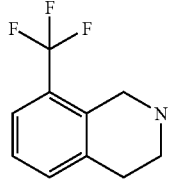

Prepared in analogy to example 1.12 (c) from 2,2,2-trifluoro-1-(8-trifluoromethyl-3,4-dihydro-1H-isoquinolin-2-yl)-ethanone (example 1.12 (b)) and sodium hydroxide.
MS (m/e): 202.2 (M+H⁺).

(b) (2-Isopropoxy-5-methanesulfonyl-phenyl)-(8-trifluoromethyl-3,4-dihydro-1H-isoquinolin-2-yl)-methanone

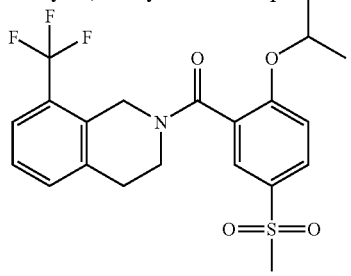

Prepared in analogy to example 1.1 from 8-trifluoromethyl-1,2,3,4-tetrahydro-isoquinoline and 2-isopropoxy-5-methanesulfonyl-benzoic acid (Example 2.1).
MS (m/e): 460.1 (M+CH₃COO⁺).

EXAMPLE 1.17

Preparation of [5-Methanesulfonyl-2-((S)-2,2,2-trifluoro-1-methyl-ethoxy)-phenyl]-(8-trifluoromethyl-3,4-dihydro-1H-isoquinolin-2-yl)-methanone

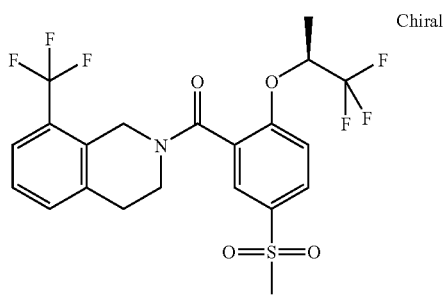

Prepared in analogy to example 1.1 from 8-trifluoromethyl-1,2,3,4-tetrahydro-isoquinoline and 5-methanesulfonyl-2-((S)-2,2,2-trifluoro-1-methyl-ethoxy)-benzoic acid (example 2.2). MS (m/e): MS (m/e): 496.4 (M+H⁺).

EXAMPLE 1.18

Preparation of (6-Chloro-3,4-dihydro-1H-isoquinolin-2-yl)-[5-methanesulfonyl-2-((S)-2,2,2-trifluoro-1-methyl-ethoxy)-phenyl]-methanone

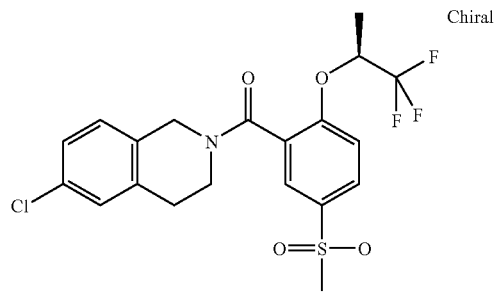

Prepared in analogy to example 1.1 from 6-chloro-1,2,3,4-tetrahydro-isoquinoline (CA [33537-99-4]) and 5-methanesulfonyl-2-((S)-2,2,2-trifluoro-1-methyl-ethoxy)-benzoic acid (example 2.2). MS (m/e): MS (m/e): 462.0 (M+H⁺).

EXAMPLE 1.19

Preparation of (6-Chloro-3,4-dihydro-1H-isoquinolin-2-yl)-(2-isopropoxy-5-methanesulfonyl-phenyl)-methanone

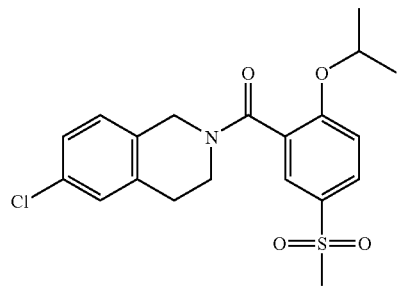

Prepared in analogy to example 1.1 from 6-chloro-1,2,3,4-tetrahydro-isoquinoline (CA [33537-99-4]) and 2-isopropoxy-5-methanesulfonyl-benzoic acid (Example 2.1).
MS (m/e): 408.0 (M+H⁺).

EXAMPLE 1.20

Preparation of 2-(2-Isopropoxy-5-methanesulfonyl-benzoyl)-1,2,3,4-tetrahydro-isoquinoline-6-carbonitrile

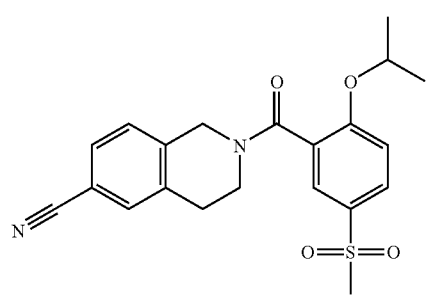

Prepared in analogy to example 1.1 from 6-cyano-1,2,3,4-tetrahydro-isoquinoline (CA [166398-34-1]) and 2-isopropoxy-5-methanesulfonyl-benzoic acid (Example 2.1).

MS (m/e): 399.4 (M+H⁺).

EXAMPLE 1.21

Preparation of (7-Dimethylamino-3,4-dihydro-1H-isoquinolin-2-yl)-(2-isopropoxy-5-methanesulfonyl-phenyl)-methanone

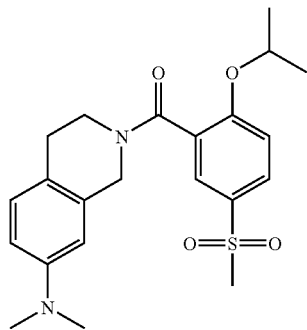

Prepared in analogy to example 1.1 from dimethyl-(1,2,3,4-tetrahydro-isoquinolin-7-yl)-amine (CA [138276-84-3]) and 2-isopropoxy-5-methanesulfonyl-benzoic acid (Example 2.1).

MS (m/e): 417.4 (M+H⁺).

EXAMPLE 1.22

Preparation of [7-(4-Chloro-benzyloxy)-3,4-dihydro-1H-isoquinolin-2-yl]-(2-isopropoxy-5-methanesulfonyl-phenyl)-methanone (a) 7-Ethoxycarbonyloxy-3,4-dihydro-1H-isoquinoline-2-carboxylic acid ethyl ester

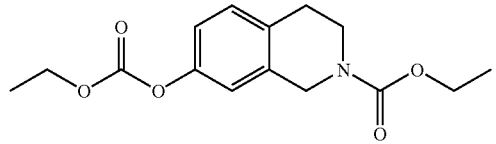

A solution of 20 mmol 1,2,3,4-tetrahydro-isoquinolin-7-ol and 140 mmol triethylamine in 300 ml tetrahydrofuran is cooled to 5° C. and treated dropwise 120 mmol chloroethyl formate. The reaction mixture is stirred overnight at room temperature, hydrolyzed with 50 ml water and extracted 3 times with diethyl ether. The organic phase is concentrated and the crude mixture purified by chromatography (SiO₂; ethyl acetate/cyclohexane 1:9) to give the title compound.
Yield=54%.

(b) 7-Hydroxy-3,4-dihydro-1H-isoquinoline-2-carboxylic acid ethyl ester

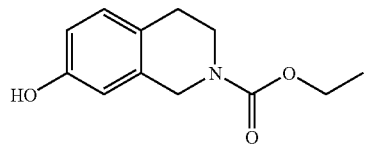

A mixture of 11 mmol 7-ethoxycarbonyloxy-3,4-dihydro-1H-isoquinoline-2-carboxylic acid ethyl ester, 14 mmol potassium carbonate, 0.6 ml water and 200 ml ethanol is stirred for 5 hours at room temperature. The reaction mixture is concentrated, diluted with 100 ml water and the pH adjusted to 7 by addition of diluted hydrochloric acid. Extraction with diethyl ether and purification by chromatography (SiO₂; ethyl acetate/cyclohexane 1:1) gives the title compound.
Yield=92%.

(c) 7-(4-Chloro-benzyloxy)-3,4-dihydro-1H-isoquinoline-2-carboxylic acid ethyl ester

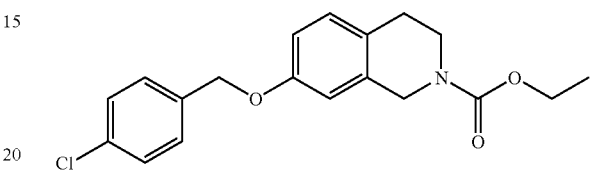

A solution of 10 mmol 7-hydroxy-3,4-dihydro-1H-isoquinoline-2-carboxylic acid ethyl ester in 25 ml N,N-dimethylformamide is treated with 20 mmol potassium carbonate, cooled to 5° C. and 12.5 mmol of 4-chlorobenzyl bromide is added. The reaction mixture is stirred for 4 hours at room temperature, quenched with water and extracted 3 times with ethyl acetate. The organic phase is dried, concentrated and purified by chromatography (SiO₂; ethyl acetate/cyclohexane 1:9) to give the title compound. Yield=71%.

(d) 7-(4-Chloro-benzyloxy)-1,2,3,4-tetrahydro-isoquinoline hydrochloride

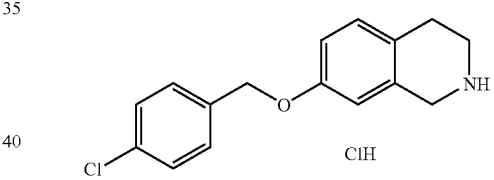

A solution of 7.2 mmol 7-(4-chloro-benzyloxy)-3,4-dihydro-1H-isoquinoline-2-carboxylic acid ethyl ester in 100 ml ethanol and 35 ml 5M aqueous sodium hydroxide is refluxed overnight. The reaction mixture is concentrated, diluted with water and acidified with conc. hydrochloric acid. The precipitate is filtered off and dried to give the title compound.
Yield=77%.

(e) [7-(4-Chloro-benzyloxy)-3,4-dihydro-1H-isoquinolin-2-yl]-(2-isopropoxy-5-methanesulfonyl-phenyl)-methanone

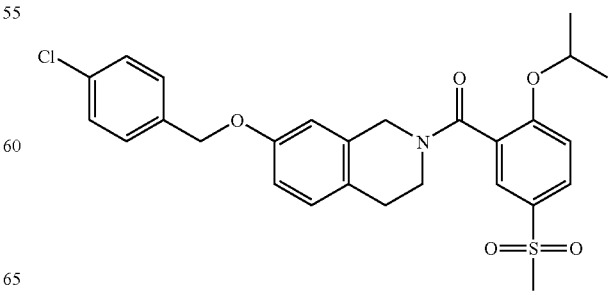

33

Prepared in analogy to example 1.1 from 7-(4-chloro-benzyloxy)-1,2,3,4-tetrahydro-isoquinoline and 2-isopropoxy-5-methanesulfonyl-benzoic acid (Example 2.1).

MS (m/e): 514.2 (M+H⁺).

EXAMPLE 1.23

Preparation of (2-Isopropoxy-5-methanesulfonyl-phenyl)-[7-(morpholine-4-sulfonyl)-3,4-dihydro-1H-isoquinolin-2-yl]-methanone

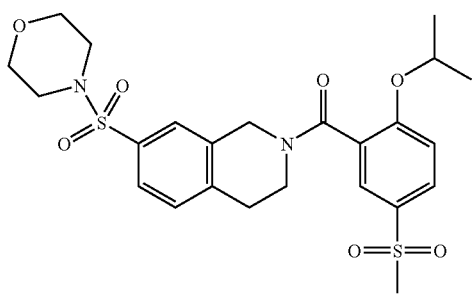

Prepared in analogy to example 1.1 from 7-(morpholine-4-sulfonyl)-1,2,3,4-tetrahydro-isoquinoline (CA [185059-05-6]) and 2-isopropoxy-5-methanesulfonyl-benzoic acid (Example 2.1). MS (m/e): 523.2 (M+H⁺).

EXAMPLE 1.24

Preparation of (6,7-Dimethoxy-3,4-dihydro-1H-isoquinolin-2-yl)-(2-isopropoxy-5-methanesulfonyl-phenyl)-methanone

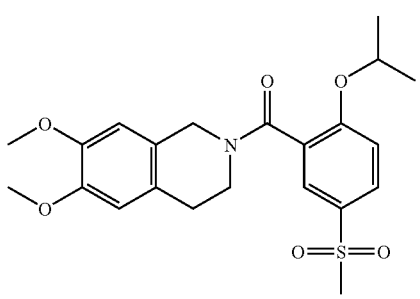

Prepared in analogy to example 1.1 from 6,7-dimethoxy-1,2,3,4-tetrahydro-isoquinoline (CA [1745-07-9]) and 2-isopropoxy-5-methanesulfonyl-benzoic acid (Example 2.1).

MS (m/e): 434.1 (M+H⁺).

34

EXAMPLE 1.25

Preparation of (7-Chloro-3,4-dihydro-1H-isoquinolin-2-yl)-(2-isopropoxy-5-methanesulfonyl-phenyl)-methanone

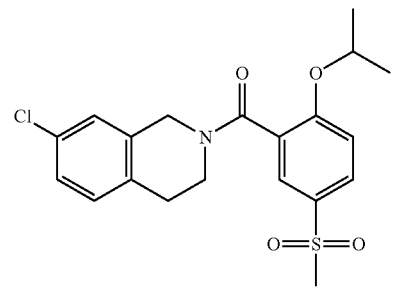

Prepared in analogy to example 1.1 from 7-chloro-1,2,3,4-tetrahydro-isoquinoline (CA [82771-60-6]) and 2-isopropoxy-5-methanesulfonyl-benzoic acid (Example 2.1).

MS (m/e): 408.1 (M+H⁺).

EXAMPLE 1.26

Preparation of (7,8-Dichloro-3,4-dihydro-1H-isoquinolin-2-yl)-(2-isopropoxy-5-methanesulfonyl-phenyl)-methanone

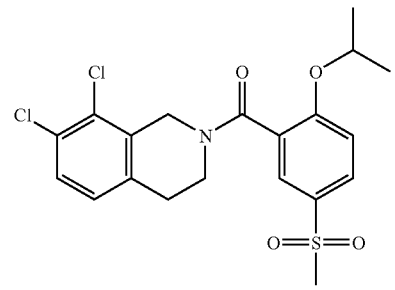

Prepared in analogy to example 1.1 from 7,8-dichloro-1,2,3,4-tetrahydro-isoquinoline (CA [61563-24-4]) and 2-isopropoxy-5-methanesulfonyl-benzoic acid (Example 2.1).

MS (m/e): 442.3 (M+H⁺).

EXAMPLE 1.27

Preparation of (2-Isopropoxy-5-methanesulfonyl-phenyl)-(7-nitro-3,4-dihydro-1H-isoquinolin-2-yl)-methanone

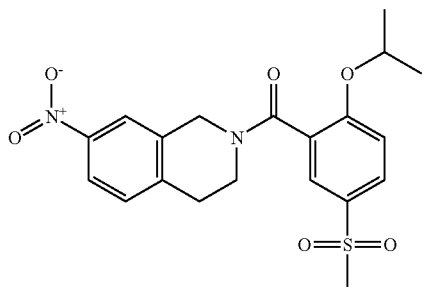

Prepared in analogy to example 1.1 from 7-nitro-1,2,3,4-tetrahydro-isoquinoline (CA [42923-79-5]) and 2-isopropoxy-5-methanesulfonyl-benzoic acid (Example 2.1).
MS (m/e): 419.3 (M+H$^+$).

EXAMPLE 1.28

Preparation of (2-Isopropoxy-5-methanesulfonyl-phenyl)-[7-(4-methyl-piperazine-1-sulfonyl)-3,4-dihydro-1H-isoquinolin-2-yl]-methanone

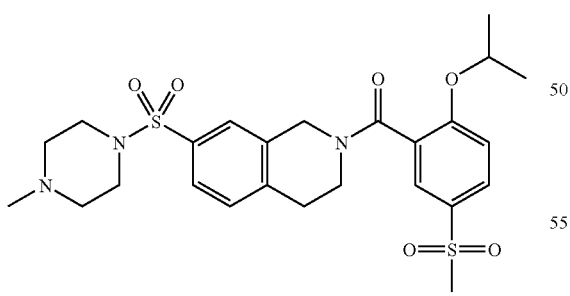

Prepared in analogy to example 1.1 from 7-(4-methyl-piperazine-1-sulfonyl)-1,2,3,4-tetrahydro-isoquinoline (CA [741674-53-3]) and 2-isopropoxy-5-methanesulfonyl-benzoic acid (Example 2.1). MS (m/e): 536.3 (M+H$^+$).

EXAMPLE 1.29

Preparation of (5-Chloro-3,4-dihydro-1H-isoquinolin-2-yl)-(2-isopropoxy-5-methanesulfonyl-phenyl)-methanone

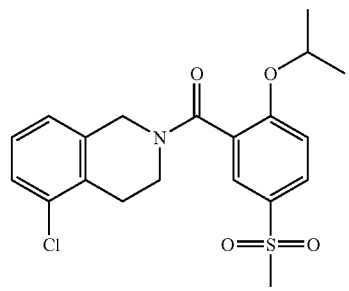

Prepared in analogy to example 1.1 from 5-chloro-1,2,3,4-tetrahydro-isoquinoline (CA [73075-43-1]) and 2-isopropoxy-5-methanesulfonyl-benzoic acid (Example 2.1).
MS (m/e): 408.0 (M+H$^+$).

EXAMPLE 1.30

Preparation of (8-Chloro-3,4-dihydro-1H-isoquinolin-2-yl)-(2-isopropoxy-5-methanesulfonyl-phenyl)-methanone

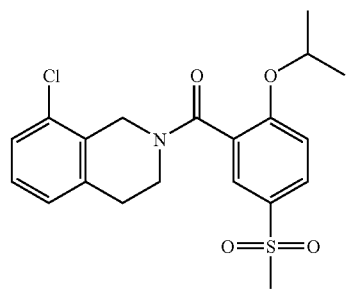

Prepared in analogy to example 1.1 from 8-chloro-1,2,3,4-tetrahydro-isoquinoline (CA [61563-33-5]) and 2-isopropoxy-5-methanesulfonyl-benzoic acid (Example 2.1).
MS (m/e): 408.3 (M+H$^+$).

EXAMPLE 1.31

Preparation of (5,7-Dichloro-3,4-dihydro-1H-isoquinolin-2-yl)-(2-isopropoxy-5-methanesulfonyl-phenyl)-methanone

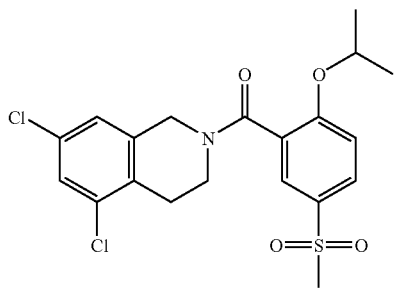

Prepared in analogy to example 1.1 from 5,7-dichloro-1,2,3,4-tetrahydro-isoquinoline (CA [89315-56-0]) and 2-isopropoxy-5-methanesulfonyl-benzoic acid (Example 2.1). MS (m/e): 442.1 (M+H$^+$).

EXAMPLE 1.32

Preparation of (3,4-Dihydro-1H-isoquinolin-2-yl)-(2-isopropoxy-5-methanesulfonyl-phenyl)-methanone

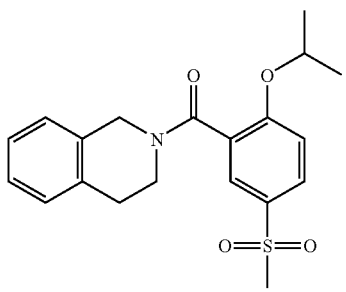

Prepared in analogy to example 1.1 from 1,2,3,4-tetrahydro-isoquinoline (CA [473443-13-9]) and 2-isopropoxy-5-methanesulfonyl-benzoic acid (Example 2.1). MS (m/e): 374.4 (M+H$^+$).

EXAMPLE 1.33

Preparation of [6-(4-Fluoro-benzyloxy)-3,4-dihydro-1H-isoquinolin-2-yl]-(2-isopropoxy-5-methanesulfonyl-phenyl)-methanone

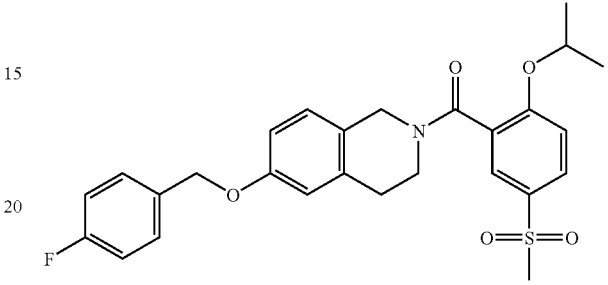

Prepared in analogy to example 1.1 from 6-(4-fluoro-benzyloxy)-1,2,3,4-tetrahydro-isoquinoline (CA [620606-78-2]) and 2-isopropoxy-5-methanesulfonyl-benzoic acid (Example 2.1). MS (m/e): 498.4 (M+H$^+$).

EXAMPLE 1.34

Preparation of (6,9-Dihydro-7H-[1,3]dioxolo[4,5-h]isoquinolin-8-yl)-(2-isopropoxy-5-methanesulfonyl-phenyl)-methanone Prepared in analogy to example 1.1 from 6,7,8,9-tetrahydro-[1,3]dioxolo[4,5-h]isoquinoline (CA [87091-23-4]) and 2-isopropoxy-5-methanesulfonyl-benzoic acid (Example 2.1). MS (m/e): 418.1 (M+H$^+$).

EXAMPLE 1.35

Preparation of (7-Bromo-3,4-dihydro-1H-isoquinolin-2-yl)-(2-isopropoxy-5-methanesulfonyl-phenyl)-methanone

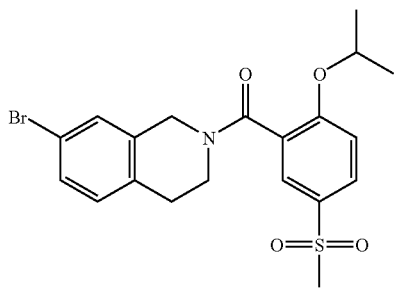

Prepared in analogy to example 1.1 from 7-bromo-1,2,3,4-tetrahydro-isoquinoline (CA [17680-55-6]) and 2-isopropoxy-5-methanesulfonyl-benzoic acid (Example 2.1).
MS (m/e): 454.2 ($\{^{81}Br\}M+H^+$), 452.1 ($\{^{79}Br\}M+H^+$).

EXAMPLE 1.36

Preparation of (6,7-Dimethoxy-4,4-dimethyl-3,4-dihydro-1H-isoquinolin-2-yl)-(2-isopropoxy-5-methanesulfonyl-phenyl)-methanone

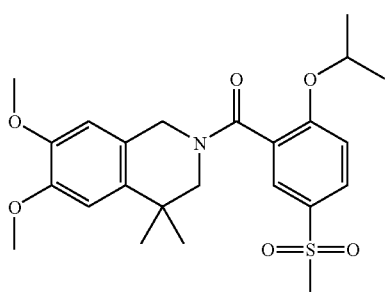

Prepared in analogy to example 1.1 from 6,7-dimethoxy-4,4-dimethyl-1,2,3,4-tetrahydro-isoquinoline (CA [57553-25-0]) and 2-isopropoxy-5-methanesulfonyl-benzoic acid (Example 2.1). MS (m/e): 462.5 (M+H$^+$).

EXAMPLE 1.37

Preparation of (4,4-Diethyl-6-methoxy-3,4-dihydro-1H-isoquinolin-2-yl)-(2-isopropoxy-5-methanesulfonyl-phenyl)-methanone

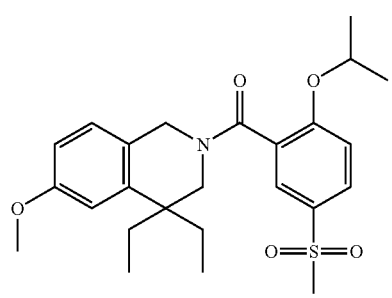

Prepared in analogy to example 1.1 from 4,4-diethyl-6-methoxy-1,2,3,4-tetrahydro-isoquinoline and 2-isopropoxy-5-methanesulfonyl-benzoic acid (Example 2.1).
MS (m/e): 460.5 (M+H$^+$).

EXAMPLE 1.38

Preparation of [6-(3-Fluoro-benzyloxy)-3,4-dihydro-1H-isoquinolin-2-yl]-(2-isopropoxy-5-methanesulfonyl-phenyl)-methanone

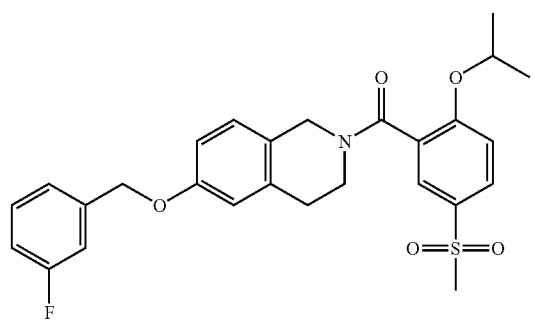

Prepared in analogy to example 1.1 from 6-(3-fluoro-benzyloxy)-1,2,3,4-tetrahydro-isoquinoline ((CA [620606-74-8]) and 2-isopropoxy-5-methanesulfonyl-benzoic acid (Example 2.1). MS (m/e): 498.4 (M+H$^+$).

EXAMPLE 1.39

Preparation of (2-Isopropoxy-5-methanesulfonyl-phenyl)-(4-methyl-3,4-dihydro-1H-isoquinolin-2-yl)-methanone

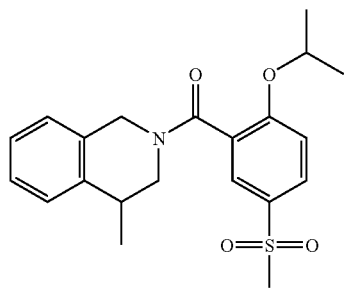

Prepared in analogy to example 1.1 from 4-methyl-1,2,3,4-tetrahydro-isoquinoline (CA [110841-71-9]) and 2-isopropoxy-5-methanesulfonyl-benzoic acid (Example 2.1).
MS (m/e): 388.4 (M+H$^+$).

Example 1.40

Preparation of (2-Isopropoxy-5-methanesulfonyl-phenyl)-(6-methoxy-3,4-dihydro-1H-isoquinolin-2-yl)-methanone

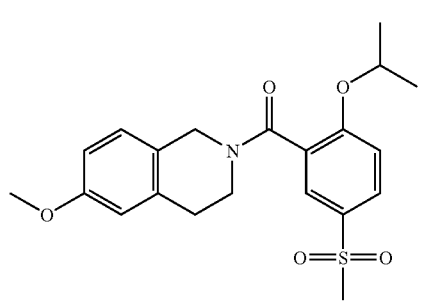

Prepared in analogy to example 1.1 from 6-methoxy-1,2,3,4-tetrahydro-isoquinoline (CA [42923-77-3]) and 2-isopropoxy-5-methanesulfonyl-benzoic acid (Example 2.1).
MS (m/e): 404.5 (M+H$^+$).

EXAMPLE 1.41

Preparation of (2-Isopropoxy-5-methanesulfonyl-phenyl)-(4-phenyl-3,4-dihydro-1H-isoquinolin-2-yl)-methanone

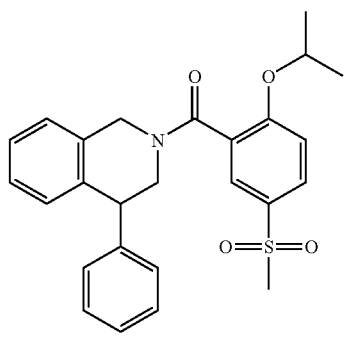

Prepared in analogy to example 1.1 from 4-phenyl-1,2,3,4-tetrahydro-isoquinoline (CA [42923-77-3]) and 2-isopropoxy-5-methanesulfonyl-benzoic acid (Example 2.1).
MS (m/e): 450.4 (M+H$^+$).

EXAMPLE 1.42

Preparation of (4-Ethyl-7-methoxy-3,4-dihydro-1H-isoquinolin-2-yl)-(2-isopropoxy-5-methanesulfonyl-phenyl)-methanone

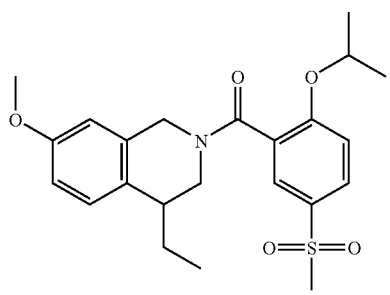

Prepared in analogy to example 1.1 from 4-ethyl-7-methoxy-1,2,3,4-tetrahydro-isoquinoline and 2-isopropoxy-5-methanesulfonyl-benzoic acid (Example 2.1).
MS (m/e): 432.5 (M+H$^+$).

EXAMPLE 1.43

Preparation of (6,8-Dimethoxy-3,4-dihydro-1H-isoquinolin-2-yl)-(2-isopropoxy-5-methanesulfonyl-phenyl)-methanone

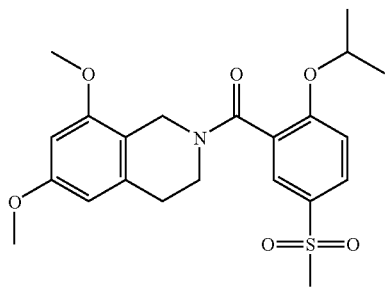

Prepared in analogy to example 1.1 from 6,8-dimethoxy-1,2,3,4-tetrahydro-isoquinoline (CA [88207-92-5]) and 2-isopropoxy-5-methanesulfonyl-benzoic acid (Example 2.1).
MS (m/e): 434.4 (M+H$^+$).

EXAMPLE 1.44

Preparation of 2-(2-Isopropoxy-5-methanesulfonyl-benzoyl)-6,7-dimethoxy-2,3-dihydro-1H-isoquinolin-4-one

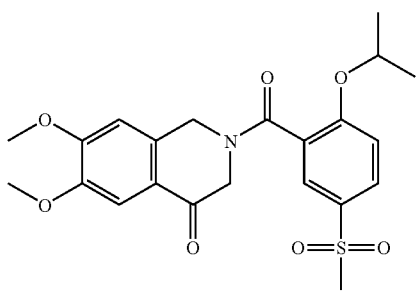

Prepared in analogy to example 1.1 from 6,7-dimethoxy-2,3-dihydro-1H-isoquinolin-4-one (CA [206763-75-9]) and 2-isopropoxy-5-methanesulfonyl-benzoic acid (Example 2.1). MS (m/e): 448.3 (M+H$^+$).

EXAMPLE 1.45

Preparation of (2-Isopropoxy-5-methanesulfonyl-phenyl)-(5-methoxy-3,4-dihydro-1H-isoquinolin-2-yl)-methanone

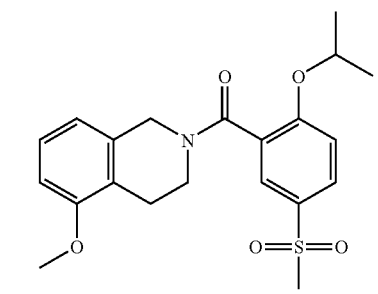

Prepared in analogy to example 1.1 from 5-methoxy-1,2,3,4-tetrahydro-isoquinoline (CA [103030-70-2]) and 2-isopropoxy-5-methanesulfonyl-benzoic acid (Example 2.1).
MS (m/e): 404.4 (M+H$^+$).

EXAMPLE 1.46

Preparation of (5-Benzyloxy-3,4-dihydro-1H-isoquinolin-2-yl)-(2-isopropoxy-5-methanesulfonyl-phenyl)-methanone

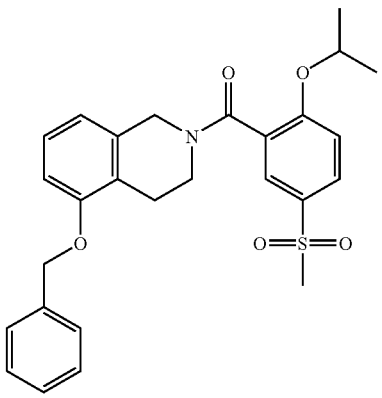

Prepared in analogy to example 1.1 from 6-benzyloxy-1,2,3,4-tetrahydro-isoquinoline (CA [189745-29-7]) and 2-isopropoxy-5-methanesulfonyl-benzoic acid (Example 2.1).
MS (m/e): 480.5 (M+H$^+$).

EXAMPLE 1.47

Preparation of (2-Isopropoxy-5-methanesulfonyl-phenyl)-(11-methyl-1,2,4,11-tetrahydro-pyrido[4,3-a]carbazol-3-yl)-methanone

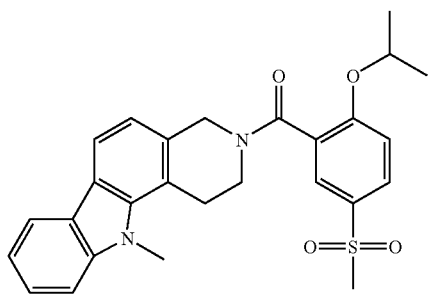

Prepared in analogy to example 1.1 from 11-methyl-2,3,4,11-tetrahydro-1H-pyrido[4,3-a] carbazole and 2-isopropoxy-5-methanesulfonyl-benzoic acid (Example 2.1).
MS (m/e): 477.4 (M+H$^+$).

EXAMPLE 1.48

Preparation of (2-Isopropoxy-5-methanesulfonyl-phenyl)-(6-methyl-3,4-dihydro-1H-isoquinolin-2-yl)-methanone

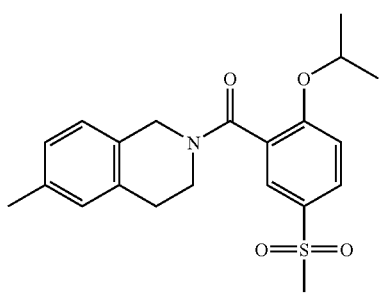

Prepared in analogy to example 1.1 from 6-methyl-1,2,3,4-tetrahydro-isoquinoline (CA [42923-76-2]) and 2-isopropoxy-5-methanesulfonyl-benzoic acid (Example 2.1).
MS (m/e): 388.4 (M+H$^+$).

EXAMPLE 1.49

Preparation of 2-(2-Isopropoxy-5-methanesulfonyl-benzoyl)-1,2,3,4-tetrahydro-isoquinoline-7-carbonitrile

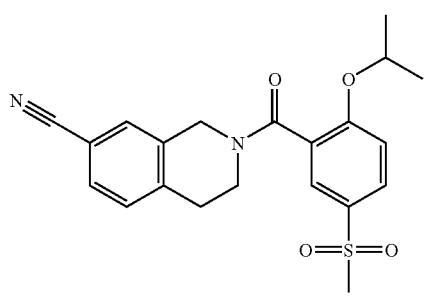

Prepared in analogy to example 1.1 from 7-cyano-1,2,3,4-tetrahydro-isoquinoline (CA [149355-52-2]) and 2-isopropoxy-5-methanesulfonyl-benzoic acid (Example 2.1).
MS (m/e): 399.1 (M+H$^+$).

EXAMPLE 1.50

Preparation of (7,8-Dihydro-5H-[1,3]dioxolo[4,5-g]isoquinolin-6-yl)-(2-isopropoxy-5-methanesulfonyl-phenyl)-methanone

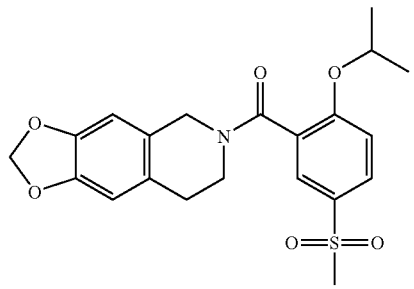

Prepared in analogy to example 1.1 from 5,6,7,8-tetrahydro-[1,3]dioxolo[4,5-g]isoquinoline (CA [94143-83-6]) and 2-isopropoxy-5-methanesulfonyl-benzoic acid (Example 2.1). MS (m/e): 418.4 (M+H$^+$).

EXAMPLE 1.51

Preparation of (2-Isopropoxy-5-methanesulfonyl-phenyl)-(7-methoxy-5-phenyl-3,4-dihydro-1H-isoquinolin-2-yl)-methanone

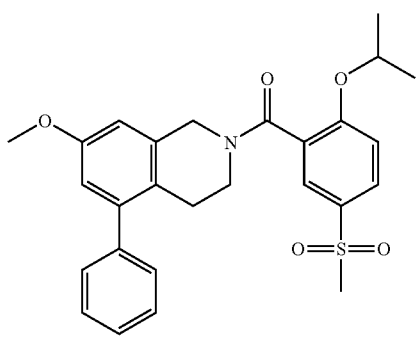

Prepared in analogy to example 1.1 from 7-methoxy-5-phenyl-1,2,3,4-tetrahydro-isoquinoline and 2-isopropoxy-5-methanesulfonyl-benzoic acid (Example 2.1).
MS (m/e): 480.5 (M+H$^+$).

EXAMPLE 1.52

Preparation of (2-Isopropoxy-5-methanesulfonyl-phenyl)-(4-methoxy-6,9-dihydro-7H-[1,3]dioxolo[4,5-h]isoquinolin-8-yl)-methanone

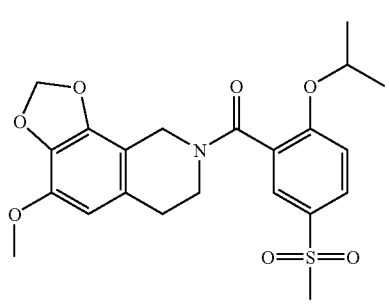

Prepared in analogy to example 1.1 from 4-methoxy-6,7,8,9-tetrahydro-[1,3]dioxolo[4,5-h]isoquinoline (CA [110103-21-4]) and 2-isopropoxy-5-methanesulfonyl-benzoic acid (Example 2.1). MS (m/e): 448.3 (M+H$^+$).

EXAMPLE 1.53

Preparation of ((4,9-Dimethyl-7,8-dihydro-5H-[1,3]dioxolo[4,5-g]isoquinolin-6-yl)-(2-isopropoxy-5-methanesulfonyl-phenyl)-methanone

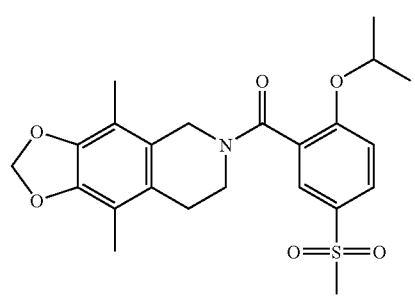

Prepared in analogy to example 1.1 from 4,9-dimethyl-5,6,7,8-tetrahydro-[1,3]dioxolo[4,5-g]isoquinoline and 2-isopropoxy-5-methanesulfonyl-benzoic acid (Example 2.1).
MS (m/e): 446.3 (M+H$^+$).

EXAMPLE 1.54

Preparation of (4-Fluoro-3,4-dihydro-1H-isoquinolin-2-yl)-(2-isopropoxy-5-methanesulfonyl-phenyl)-methanone

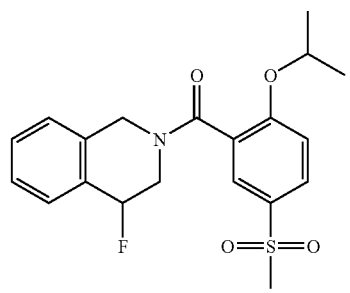

Prepared in analogy to example 1.1 from 4-fluoro-1,2,3,4-tetrahydro-isoquinoline (CA [537033-79-7]) and 2-isopropoxy-5-methanesulfonyl-benzoic acid (Example 2.1). MS (m/e): 392.0 (M+H$^+$).

EXAMPLE 1.55

Preparation of (3,4-Dihydro-2H-quinolin-1-yl)-(2-isopropoxy-5-methanesulfonyl-phenyl)-methanone

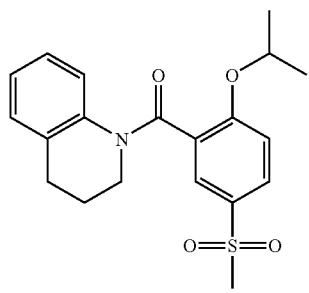

Prepared in analogy to example 1.1 from 1,2,3,4-tetrahydro-quinoline (CA [635-46-1]) and 2-isopropoxy-5-methanesulfonyl-benzoic acid (Example 2.1). MS (m/e): 373.3 (M+).

Example 1.56

Preparation of (6-Chloro-3,4-dihydro-1H-isoquinolin-2-yl)-(2-diethylamino-5-methanesulfonyl-phenyl)-methanone

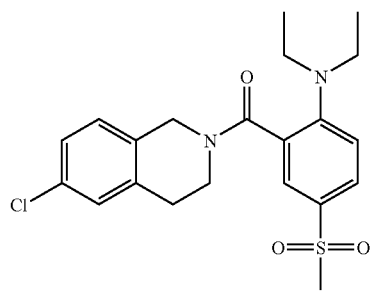

Prepared in analogy to example 1.1 from 6-chloro-1,2,3,4-tetrahydro-isoquinoline (CA [33537-99-4]) and 2-diethylamino-5-methanesulfonyl-benzoic acid (example 2.6).
MS (m/e): 421.1 (M+H+).

EXAMPLE 1.57

Preparation of (6-Chloro-3,4-dihydro-1H-isoquinolin-2-yl)-(2-isopropylsulfanyl-5-methanesulfonyl-phenyl)-methanone

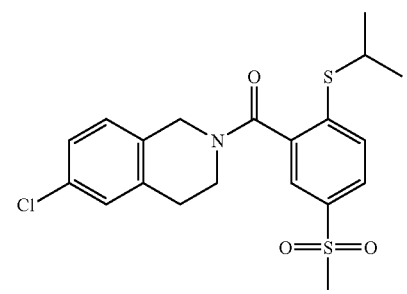

Prepared in analogy to example 1.1 from 6-chloro-1,2,3,4-tetrahydro-isoquinoline (CA [33537-99-4]) and 2-isopropylsulfanyl-5-methanesulfonyl-benzoic acid (example 2.7). MS (m/e): 424.1 (M+H+).

EXAMPLE 1.58

Preparation of (6-Chloro-3,4-dihydro-1H-isoquinolin-2-yl)-(2-morpholin-4-yl-5-nitro-phenyl)-methanone

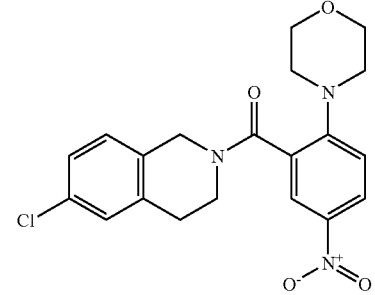

Prepared in analogy to example 1.1 from 6-chloro-1,2,3,4-tetrahydro-isoquinoline (CA [33537-99-4]) and 2-morpholin-4-yl-5-nitro-benzoic acid (example 2.8).
MS (m/e): 402.3 (M+H+).

EXAMPLE 1.59

Preparation of (6-Chloro-3,4-dihydro-1H-isoquinolin-2-yl)-(2-cyclopropylmethoxy-5-methanesulfonyl-phenyl)-methanone

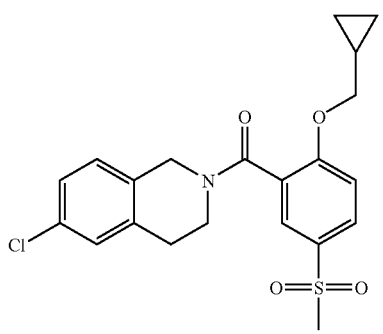

Prepared in analogy to example 1.1 from 6-chloro-1,2,3,4-tetrahydro-isoquinoline (CA [33537-99-4]) and 2-cyclopropylmethoxy-5-methanesulfonyl-benzoic acid (example 2.9). MS (m/e): 420.1 (M+H⁺).

EXAMPLE 1.60

Preparation of (2-Isopropoxy-5-methanesulfonyl-phenyl)-(6-methoxy-3,4-dihydro-2H-quinolin-1-yl)-methanone

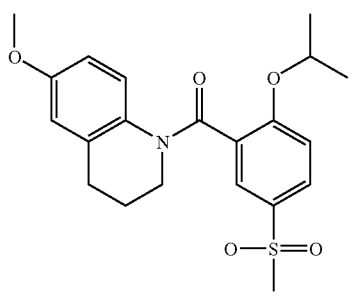

Prepared in analogy to example 1.1 from 6-methoxy-1,2,3,4-tetrahydro-quinoline (CA [120-15-0]) and 2-isopropoxy-5-methanesulfonyl-benzoic acid (Example 2.1).
MS (m/e): 404.2 (M+H⁺).

EXAMPLE 1.61

Preparation of (2-Isopropoxy-5-methanesulfonyl-phenyl)-(6-methyl-3,4-dihydro-2H-quinolin-1-yl)-methanone

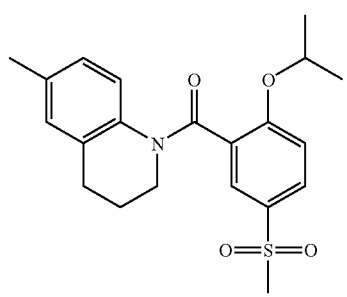

Prepared in analogy to example 1.1 from 6-methyl-1,2,3,4-tetrahydro-quinoline (CA [91-61-2]) and 2-isopropoxy-5-methanesulfonyl-benzoic acid (Example 2.1). MS (m/e): 445.9 (M+CH3COOH).

EXAMPLE 1.62

Preparation of (7-Chloro-3,4-dihydro-2H-quinolin-1-yl)-(2-isopropoxy-5-methanesulfonyl-phenyl)-methanone

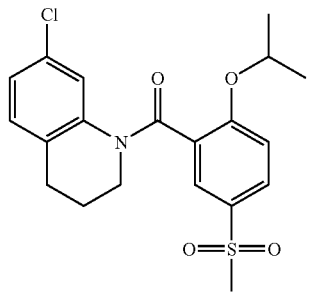

Prepared in analogy to example 1.1 from 7-chloro-1,2,3,4-tetrahydro-quinoline (CA [90562-35-9]) and 2-isopropoxy-5-methanesulfonyl-benzoic acid (Example 2.1).
MS (m/e): 408.1 (M+H⁺).

EXAMPLE 1.63

Preparation of (2-Isopropoxy-5-methanesulfonyl-phenyl)-(7-trifluoromethyl-3,4-dihydro-2H-quinolin-1-yl)-methanone

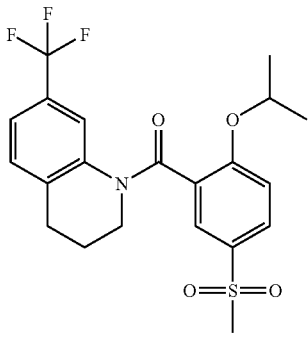

Prepared in analogy to example 1.1 from 7-trifluoromethyl-1,2,3,4-tetrahydro-quinoline (CA [450-62-4]) and 2-isopropoxy-5-methanesulfonyl-benzoic acid (Example 2.1).
MS (m/e): 500.1 (M+CH3COOH).

EXAMPLE 2.1

Preparation of 2-Isopropoxy-5-methanesulfonyl-benzoic acid (a) 2-Chloro-5-methanesulfonyl-benzoic acid

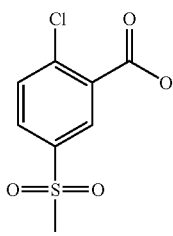

To 99 mmol 2-chloro-5-(methylthio) benzoic acid in 400 ml methanol at 0° C. 296 mmol Oxone® was added and the mixture was allowed to stir at RT for 3.5 h. The precipitate was filtered off and the filtrate was concentrated under reduced pressure. The residue was extracted 3× with 400 ml ethyl acetate and the combined organic phases washed 2× with 300 ml 1N HCl and with 300 ml saturated aqueous NaCl solution and dried with MgSO₄. Evaporation under reduced pressure yielded the title compound.

(b) 2-Isopropoxy-5-methanesulfonyl-benzoic acid

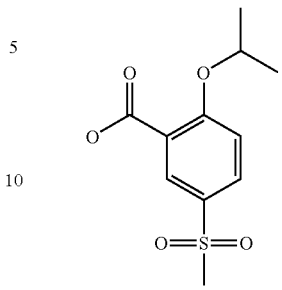

A mixture of 2.13 mmol 2-chloro-5-methanesulfonyl-benzoic acid, 0.64 mmol Cu(I)Br in 5 ml NEt₃ and 25 ml isopropanol was heated to 120° C. for 16 h in a sealed tube. The volatiles were removed under vacuum and the residue was taken up in 70 ml 1N HCl. Extraction with ethyl acetate drying of the combined organic fractions and evaporation yielded a residue which was purified by reversed phase preparative HPLC eluting with an acetonitrile/water gradient. Evaporation of the product fractions yielded the title compound.
MS (m/e): 257.0 (M−H⁺, 100%)

EXAMPLE 2.2

Preparation of 5-Methanesulfonyl-2-((S)-2,2,2-trifluoro-1-methyl-ethoxy)-benzoic acid (a) rac-5-Methanesulfonyl-2-(2,2,2-trifluoro-1-methyl-ethoxy)-benzoic acid methyl ester

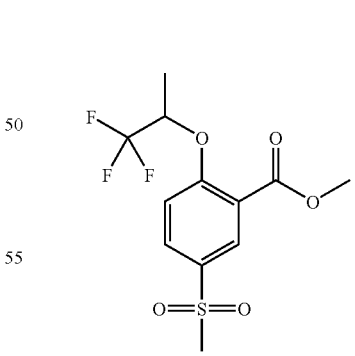

A mixture of 21.7 mmol 2-hydroxy-5-methanesulfonyl-benzoic acid methyl ester [68029-77-6], 32.5 mmol trifluoromethanesulfonic acid 2,2,2-trifluoro-1-methyl-ethyl ester [212556-43-9], 43.4 mmol potassium carbonate in 87 ml DMF was stirred at 80° C. for 48 hour After cooling to RT, the mixture was concentrated in vacuo, taken in water and stirred for 1 hour. Filtration yielded the title compound.

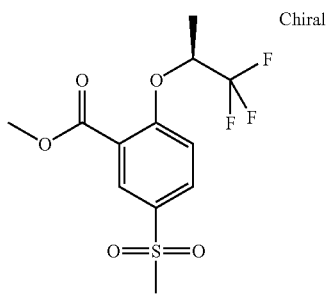

The title compound was obtained by separation of rac-5-methanesulfonyl-2-(2,2,2-trifluoro-1-methyl-ethoxy)-benzoic acid methyl ester by chiral HPLC (Chiralcel OD, 15% ethanol/heptane, flow 35 ml, 220 nm, retention time: 86 min.).

(c) 5-Methanesulfonyl-2-((S)-2,2,2-trifluoro-1-methyl-ethoxy)-benzoic acid

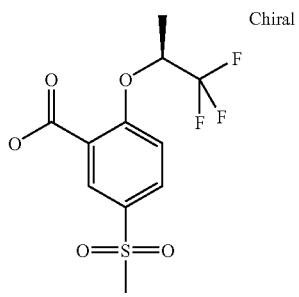

Prepared from 5-methanesulfonyl-2-((S)-2,2,2-trifluoro-1-methyl-ethoxy)-benzoic acid methyl ester by saponification with excess 1N NaOH at 60° for 15 minutes. Acidification of the reaction mixture with 1N HCl yields the title compound.

MS (m/e): 311.0 (M–H$^+$, 100%)

EXAMPLE 2.3

Preparation of 5-Methanesulfonyl-2-((R)-2,2,2-trifluoro-1-methyl-ethoxy)-benzoic acid (a) 5-Methanesulfonyl-2-((R)-2,2,2-trifluoro-1-methyl-ethoxy)-benzoic acid methyl ester

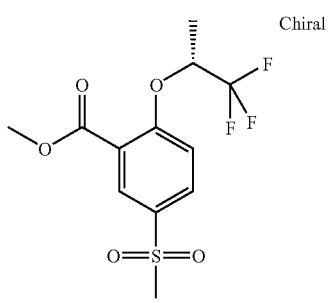

The title compound was obtained by separation of rac-5-methanesulfonyl-2-(2,2,2-trifluoro-1-methyl-ethoxy)-benzoic acid methyl ester by chiral HPLC (Chiralcel OD, 15% ethanol/heptane, flow 35 ml, 220 nm, retention time: 74 min).

(b) 5-Methanesulfonyl-2-((R)-2,2,2-trifluoro-1-methyl-ethoxy)-benzoic acid

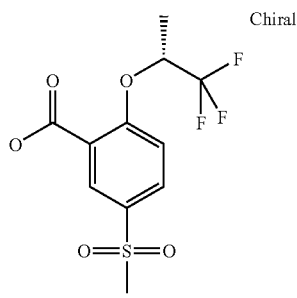

The compound was prepared in analogy to compound 2.2 (c) from 5-methanesulfonyl-2-((R)-2,2,2-trifluoro-1-methyl-ethoxy)-benzoic acid methyl ester MS (m/e): 311.0 (M–H$^+$, 100%)

EXAMPLE 2.4

Preparation 5-Methanesulfonyl-2-morpholin-4-yl-benzoic acid (a) 2-Chloro-5-methanesulfonyl-benzoic acid

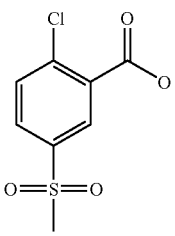

A solution of 2-chloro-5-(methylthio)benzoic acid (CAS: 51546-12-4; 2.5 g, 11.8 mmol) was dissolved in methanol (50 ml) and cooled to 0° C. Oxone® (21.9 g, 35.5 mmol) was added portionwise within 5 minutes. The mixture was stirred at 0° C. for 30 minutes and then at room temperature for 22 hours. The mixture was filtered. The filtrate was poured onto water (200 ml).

The aqueous layer was extracted with dichloromethane (5×50 ml). The combined extracts were dried over Na$_2$SO$_4$, filtered and the solvent was removed in vacuo. The solid was stirred in ether (30 ml), filtered and dried to provide the title compound (1.96 g, 70%) as a beige solid, MS (m/e): 232.9 (M–H$^+$, 100%).

(b) 5-Methanesulfonyl-2-morpholin-4-yl-benzoic acid
(b) 5-Methanesulfonyl-2-((S)-2,2,2-trifluoro-1-methyl-ethoxy)-benzoic acid methyl ester

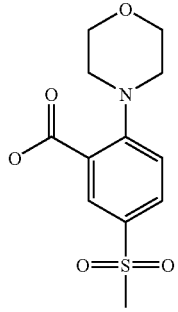

A mixture of 163.8 mg (0.7 mmol) 2-chloro-5-methane-sulfonyl-benzoic acid in 2 ml morpholine was heated for 16 h to 100° C. After evaporation of all volatiles the residue was taken up in 2 ml methanol/formic acid 3/1 and subjected to reversed phase HPLC purification eluting with an acetonitrile/water gradient to yield the title compound after evaporation of the product fractions. MS (m/e): 284.1 (MH⁻, 100%).

EXAMPLE 2.5

Preparation
4-Methanesulfonyl-biphenyl-2-carboxylic acid (a) 2-Amino-5-methanesulfonyl-benzoic acid

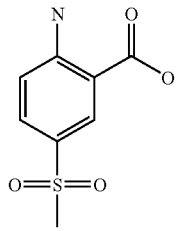

A mixture of 4.26 mmol 2-chloro-5-methanesulfonyl-benzoic acid, 0.39 mmol Copper powder and 10 ml ammonium hydroxide 25% was heated at 125-130° C. with stirring for 18 hours. Mixture was cooled to room temperature and filtered. The solid was washed with methanol. The filtrate was concentrated in vacuo. The residue was acidified with HCl 1N to pH=2. The obtained solid was washed with water and dried (HV, 50° C., 1 hour) to yield the title compound. MS (m/e): 214.1 (M–H⁺, 100%)

(b) 2-Iodo-5-methanesulfonyl-benzoic acid

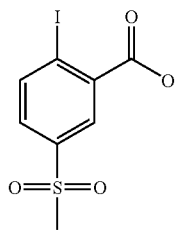

To a suspension of 3.0 mmol 2-amino-5-methanesulfonyl-benzoic acid in a mixture of 1.7 ml sulfuric acid and 1.7 ml water was added dropwise a solution of 3.92 mmol sodium nitrite in 1.7 ml water at such rate that the temperature did not exceed 3° C. The mixture was stirred at 0° C. for 1 hour. A solution of 3.0 mmol KI in 1.7 ml water was added dropwise at 0° C. The brown suspension was allowed to warm to rt and stirred for 30 minutes. Excess iodine was destroyed by addition of a few drops of a sodium hydrogenosulfite solution. The solid was filtered, washed with water and dried (HV, 50° C., 1 hour) to yield the title compound. MS (m/e): 325.0 (M–H, 100%)

(c) 4-Methanesulfonyl-biphenyl-2-carboxylic acid

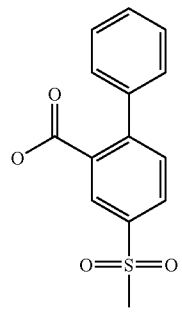

A mixture of 15 mmol 2-iodo-5-methanesulfonyl-benzoic acid, 31 mmol phenylboronic acid, 45 mmol sodium carbonate and 34 mg palladium(II)-acetate in 100 ml water is stirred at room temperature for 60 hours. The reaction mixture is acidified by careful addition of concentrated hydrochloric acid and extracted 3 times with ethyl acetate. The organic phase is dried, concentrated and the residue crystallized from diethyl ether to yield the title compound (3.87 g, 91%) as a slightlyyellow solid, MS (m/e): 275.0 (M–H⁺, 100%).

EXAMPLE 2.6

Preparation of
2-Diethylamino-5-methanesulfonyl-benzoic acid

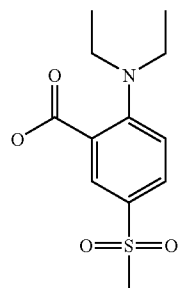

3.0 g of 2-fluoro-5-methanesulfonyl-benzoic acid (CA 247569-56-8; WO200501453) was dissolved in 30 ml of diethylamine and refluxed overnight. The reaction mixture was diluted with water, acidified by addition of diluted hydrochloric acid and extracted with ethyl acetate. The organic phase was dried and concentrated to give the title compound as a slightly brownish solid. MS (m/e): 272.1 (M+H⁺; 100%)

EXAMPLE 2.7

Preparation of 2-Isopropylsulfanyl-5-methanesulfonyl-benzoic acid

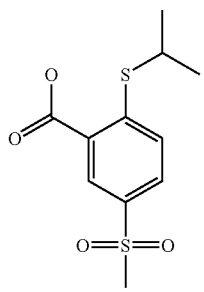

a) 2-Fluoro-5-methylsulfanyl-benzoic acid

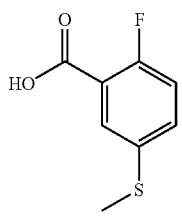

The title compound was prepared by following the procedure described in: Journal of Organometallic Chemistry 1991, 419(1-2), 1-8.

b) 2-Fluoro-5-methanesulfonyl-benzoic acid

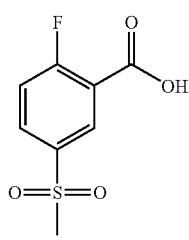

To 2.68 mmol 2-fluoro-5-methanesulfanyl-benzoic acid in 5 ml methanol at 0° C. was added 8.05 mmol Oxone® and the mixture was allowed to stir at RT for 72 h. The precipitate was filtered off and the filtrate was concentrated under reduced pressure. The residue was treated with water and extracted 3 times with 400 ml dichloromethane. The combined organic phases were dried over sodium sulfate. Evaporation under reduced pressure yielded the title compound as a white crystalline solid (yield 79%). MS (m/e): 217.2 (M–H$^+$, 100%).

c) 2-Isolpropylsulfanyl-5-methanesulfonyl-benzoic acid

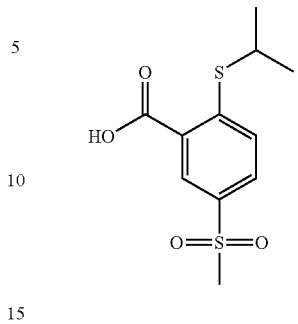

To a solution of 4.58 mmol 2-fluoro-5-methanesulfonyl-benzoic acid in 6 ml N,N-dimethylacetamide were added 15.2 mol cesium carbonate and 10.1 mmol 2-propanethiol and the mixture was stirred at 90° C. for 3 h. The reaction mixture was then cooled to room temperature and acidified to pH1 by addition of hydrochloric acid before being extracted three times with ethyl acetate. The combined organic phases were dried over sodium sulfate and concentrated in vacuo to afford the title compound as a light yellow liquid which was used in the next step without further purification (yield 99%). EI-MS (m/e): 274.1 (M$^+$, 35%), 232.1 ([M-C$_3$H$_6$]$^+$, 30%, 214.1 (M-C$_3$H$_6$—H$_2$O)$^+$, 100%).

EXAMPLE 2.8

Preparation of 2Morpholin-4-yl-5-nitro-benzoic acid

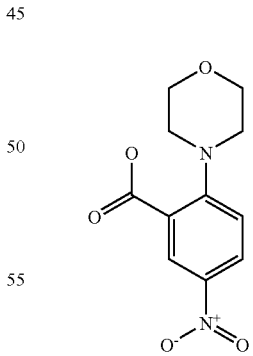

To a solution of 2-fluoro-5-nitrobenzoic acid (4.86 g, 26.2 mmol) in dioxane (50 ml) was added morpholine (11.5 ml). The mixture was stirred at room temperature for 2 hours. The solvent was removed in vacuo. The residue was dissolved in water and the mixture was acidified with HCl 2N. The solid was filtered, washed with water and dried to provide the title compound (6.2 g, 93%) as a yellow solid, MS (m/e): 251.2 (M–H, 100%).

EXAMPLE 2.9

Preparation of
2-Cyclopropylmethoxy-5-methanesulfonyl-benzoic acid

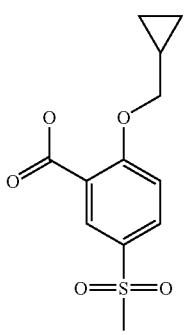

This compound (CA 845616-03-7) was prepared as described in WO2005014563.

MS (m/e): 269.1 (MH⁻, 89%)

The invention claimed is:
1. A compound of formula IA-4

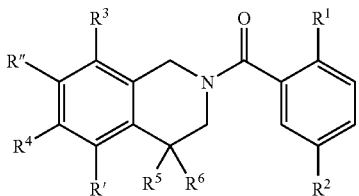

wherein
R$^1$ is aryl, a cyclic amine selected from the group consisting of pyrrol-1-yl, piperidin-1-yl, piperazin-1-yl, morpholin-4-yl, thiomorpholin-4-yl, 1-oxo-thiomorpholin-4-yl and 1, 1-dioxo-thiomorpholin-4-yl, OR$^{11}$, SR$^{11}$, or N(R$^{12}$)$_2$;
R$^{11}$ is lower alkyl, lower alkyl substituted by halogen, or —(CH$_2$)$_n$-cycloalkyl;
each R$^{12}$ is independently hydrogen or lower alkyl;
R$^2$ is NO$_2$, CN or S(O)$_2$-lower alkyl;
R$^3$ is hydrogen, halogen, lower alkyl, lower alkyl substituted by halogen, or lower alkoxy;
R$^4$ is hydrogen, halogen, lower alkyl, lower alkyl substituted by halogen, non cyclic amine, lower alkoxy, or benzyloxy optionally substituted by halogen;
R$^5$ and R$^6$ are each independently hydrogen, halogen, lower alkyl, lower alkoxy, aryl or form together the keto group =O;
R' is hydrogen, halogen, lower alkyl, lower alkoxy, or benzyloxy optionally substituted by halogen;
R" is hydrogen; alkyl substituted by halogen; halogen; nitro; lower alkoxy; cyano; COO-lower alkyl; benzyloxy optionally substituted by halogen; or S(O)$_2$-cyclic amine, wherein the cyclic amine is selected from the group consisting of pyrrol-1-yl, piperidin-1-yl, piperazin-1-yl, morpholin-4-yl, thiomorpholin-4-yl, 1-oxo-thiomorpholin-4-yl and 1,1-dioxo-thiomorpholin-4-yl; or
R$^3$ and R" or R$^4$ and R' or R" and R$^4$ are together with the carbon atom to which they are attached —O—(CH$_2$)$_n$—O— or —O—(CH$_2$)$_m$— or —(CH$_2$)$_m$—O—, or n is 1 or 2; and
m is 2 or 3;
or a pharmaceutically acceptable acid addition salt thereof.
2. A compound of claim 1, wherein at least one of R$^3$, R", R$^4$ or R' is halogen.
3. A compound of claim 2, selected from the group consisting of
(6-chloro-3,4-dihydro-1H-isoquinolin-2-yl)-[5-methanesulfonyl-2-((S)-2,2,2-trifluoro-1-methyl -ethoxy)-phenyl]-methanone,
(6-chloro-3,4-dihydro-1H-isoquinolin-2-yl)-(2-isopropoxy-5-methanesulfonyl-phenyl)-methanone,
(7-chloro-3,4-dihydro-1H-isoquinolin-2-yl)-(2-isopropoxy-5-methanesulfonyl-phenyl)-methanone,
(7,8-dichloro-3,4-dihydro-1H-isoquinolin-2-yl)-(2-isopropoxy-5-methanesulfonyl-phenyl) -methanone and
(8-chloro-3,4-dihydro-1H-isoquinolin-2-yl)-(2-isopropoxy-5-methanesulfonyl-phenyl)-methanone.
4. A compound of claim 1, wherein at least one of R$^3$, R", R$^4$ or R' is alkyl substituted by halogen.
5. A compound of claim 4, selected from the group consisting of
(2-isopropoxy-5-methanesulfonyl-phenyl)-(6-trifluoromethyl-3,4-dihydro-1H-isoquinolin-2-yl) -methanone,
(5-methanesulfonyl-2-morpholin-4-yl-phenyl)-(6-trifluoromethyl-3,4-dihydro-1H-isoquinolin-2-yl)-methanone,
[5-methanesulfonyl-2-((S)-2,2,2-trifluoro-1-methyl-ethoxy)-phenyl]-(6-trifluoromethyl-3, 4-dihydro-1H-isoquinolin-2-yl)-methanone and
(4-methanesulfonyl-biphenyl-2-yl)-(6-trifluoromethyl-3, 4-dihydro-1H-isoquinolin-2-yl) -methanone.
6. A compound of claim 1, wherein at least one of R" is CN.
7. A compound of claim 6, which is
2-(2-isopropoxy-5-methanesulfonyl-benzoyl)-1,2,3,4-tetrahydro-isoquinoline-6-carbonitrile.
8. A compound of claim 1, wherein at least one of R$^3$, R", R$^4$ or R' is lower alkoxy.
9. A compound of claim 8, which is
(2-isopropoxy-5-methanesulfonyl-phenyl)-(6-methoxy-3, 4-dihydro-1H-isoquinolin-2-yl) -methanone.
10. A compound of claim 1, wherein R$^1$ is S-lower alkyl.
11. A compound of claim 10, wherein the compound is (6-chloro-3,4-dihydro-1H-isoquinolin-2-yl)-(2-isopropylsulfanyl-5-methanesulfonyl-phenyl) -methanone.
12. A compound of claim 1, wherein one of R$^3$ and R" or R$^4$ and R' or R" and R$^4$ are together with the carbon atom to which they are attached

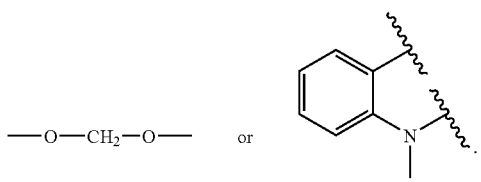

13. A compound of claim 12, selected from the group consisting of
(2-isopropoxy-5-methanesulfonyl-phenyl)-(11-methyl-1,2,4,11-tetrahydro-pyrido[4,3-a]carbazol-3-yl)-methanone and
((4,9-dimethyl-7,8-dihydro-5H-[1,3]dioxolo[4,5-g]isoquinolin-6-yl)-(2-isopropoxy-5-methanesulfonyl-phenyl)-methanone.

14. A compound of claim 1, wherein $R^2$ is $SO_2CH_3$.

15. A compound of claim 14, wherein $R^1$ is $OR^{11}$.

16. A compound of claim 14, wherein $R^1$ is aryl.

17. A compound of claim 16, wherein $R^1$ is phenyl.

18. A compound of claim 14, wherein $R^1$ is a cyclic amine selected from the group consisting of pyrrol-1-yl, piperidin-1-yl, piperazin-1-yl, morpholin-4-yl, thiomorpholin-4-yl, 1-oxo-thiomorpholin-4-yl and 1,1-dioxo-thiomorpholin-4-yl.

19. A pharmaceutical composition comprising a compound of formula IA-4

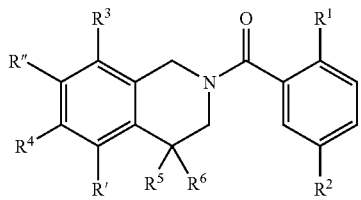

IA-4 wherein
$R^1$ is aryl, a cyclic amine selected from the group consisting of pyrrol-1-yl, piperidin-1-yl, piperazin-1-yl, morpholin-4-yl, thiomorpholin-4-yl, 1-oxo-thiomorpholin-4-yl and 1,1-dioxo-thiomorpholin-4-yl, $OR^{11}$, $SR^{11}$ or $N(R^{12})_2$;

$R^{11}$ is lower alkyl, lower alkyl substituted by halogen, or —$(CH_2)_n$-cycloalkyl;

each $R^{12}$ is independently hydrogen or lower alkyl;

$R^2$ is $NO_2$, CN or $S(O)_2$-lower alkyl;

$R^3$ is hydrogen, halogen, lower alkyl, lower alkyl substituted by halogen, or lower alkoxy;

$R^4$ is hydrogen, halogen, lower alkyl, lower alkyl substituted by halogen, non cyclic amine, lower alkoxy, or benzyloxy optionally substituted by halogen;

$R^5$ and $R^6$ are each independently hydrogen, halogen, lower alkyl, lower alkoxy, aryl or form together the keto group =O;

R' is hydrogen, halogen, lower alkyl, lower alkoxy, or benzyloxy optionally substituted by halogen;

R" is hydrogen, alkyl substituted by halogen, halogen, nitro, lower alkoxy, cyano, COO-lower alkyl, benzyloxy optionally substituted by halogen, or $S(O)_2$-cyclic amine; wherein the cyclic amine is selected from the group consisting of pyrrol-1-yl, piperidin-1-yl, piperazin-1-yl, morpholin-4-yl, thiomorpholin-4-yl, 1-oxo-thiomorpholin-4-yl and 1,1-dioxo-thiomorpholin-4-yl; or $R^3$ and R" or $R^4$ and R' or R" and $R^4$ are together with the carbon atom to which they are attached —O—$(CH_2)_n$—O— or —O—$(CH_2)_m$— or —$(CH_2)_m$—O—, or

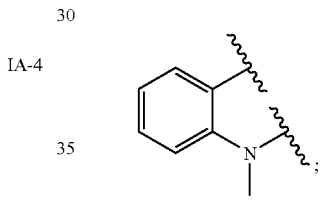

n is 1 or 2; and
m is 2 or 3;
or a pharmaceutically acceptable acid addition salt thereof and a pharmaceutically acceptable carrier.

* * * * *